United States Patent [19]
Sauer et al.

[11] Patent Number: 5,972,898
[45] Date of Patent: Oct. 26, 1999

[54] 3',3-N-BIS-SUBSTITUTED MACROLIDE LHRH ANTAGONISTS

[75] Inventors: Daryl R. Sauer, Trevor, Wis.; Fortuna Haviv, Deerfield, Ill.; John Randolph, Mundelein, Ill.; Nicholas A. Mort, Waukegan, Ill.; Christopher R. Dalton, Mundelein, Ill.; Milan Bruncko, Lake Bluff, Ill.; Michele A. Kaminski, Beach Park, Ill.; Bradley W. Crawford, Gurnee, Ill.; Lisa Marie Frey, Mundelein, Ill.; Jonathan Greer, Chicago, Ill.

[73] Assignee: Abbott Laboratories, Abbott Park, Ill.

[21] Appl. No.: 09/049,458

[22] Filed: Mar. 27, 1998

[51] Int. Cl.$^6$ ............... A61K 31/70; C07H 1/00; C07H 17/08

[52] U.S. Cl. ............... 514/29; 536/7.2; 536/7.4; 536/18.5

[58] Field of Search ............... 514/29; 536/7.2, 536/7.4, 18.5

[56] References Cited

U.S. PATENT DOCUMENTS 4,677,097  6/1987  Omura et al. ............... 514/29

FOREIGN PATENT DOCUMENTS

| 0215355 A2 | 3/1987 | European Pat. Off. . |
| 0248279 A2 | 12/1987 | European Pat. Off. . |
| 0349100 A2 | 1/1990 | European Pat. Off. . |
| 0559896 A1 | 9/1993 | European Pat. Off. . |

OTHER PUBLICATIONS

Chem. Pharm. Bull, vol. 37, No. 10 (1989), pp. 2701–2709, T. Sunazuka et al.

*Primary Examiner*—Elli Peselev
*Attorney, Agent, or Firm*—Mona Anand

[57] ABSTRACT

Disclosed are 3',3'-N-bisdesmethyl-3',3'-N-bis-substituted-6-O-methyl-11-deoxy-11,12-cyclic carbamate erythromycin A derivatives which are antagonists of lutenizing hormone-releasing hormone (LHRH). Also disclosed are pharmaceutical compositions comprising the compounds, to methods of using the compounds and to the process of making the same.

16 Claims, No Drawings

3',3-N-BIS-SUBSTITUTED MACROLIDE LHRH ANTAGONISTS

TECHNICAL FIELD

The present invention relates to a class of macrolide compounds which are antagonists of lutenizing hormone-releasing hormone (LHRH), to pharmaceutical compositions comprising the compounds, to methods of using the compounds and to the process of making the same. More particularly, the present invention relates to 3',3'-N-bis-desmethyl-3',3'-N-bis-substituted-6-O-methyl-11-deoxy-11,12-cyclic carbamate erythromycin A derivatives which are antagonists of LHRH.

BACKGROUND OF THE INVENTION

The gonadotropins, follicle stimulating hormone (FSH), lutenizing hormone (LH), and chorionic gonadotropin (CG) are required for ovulation, spermatogenesis, and the biosynthesis of sex steroids. A single hypothalamic hormone, gonadotropin-releasing hormone (GnRH) also known as LHRH is responsible for regulating the secretion of both FSH and LH in mammals.

LHRH is a decapeptide having the structure:

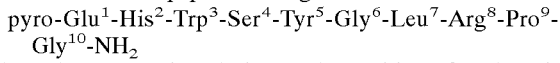

where the superscripts designate the position of each aminoacyl residue in the decapeptide chain.

LHRH is released from the hypothalamus and binds to a receptor on the pituitary gland, causing the release of LH and FSH which subsequently act on the gonads to stimulate the synthesis of steroid sex hormones. The pulsatile release of LHRH, and thereby the release of LH and FSH, controls the reproductive cycle in animals and humans. Acute doses of LHRH agonists increase the levels of LH and steroidal sex hormones in both animals and humans. Paradoxically, chronic doses of LHRH agonists suppress the level of LH and steroidal sex hormones. Consequently, the effect of multiple doses of LHRH agonists is to suppress estrogen formation in females and testosterone production in males. The same effect is observed in both animals and humans after administration of either acute or chronic doses of LHRH antagonists.

In recent years considerable research effort has been expended on finding antagonists of LHRH. These efforts have produced a number of peptide LHRH antagonists, which suppress LH and reproductive hormones in mammals upon acute or chronic administration. See for example, M. J. Karten in "Modes of Action of GnRH and GnRH analogs", edited by W. F. Crowley and P. M. Conn, p. 277 (1992). The literature has reported that LHRH antagonists are useful in the treatment of a variety of conditions in which the suppression of sex steroids plays a key role including contraception, delay of puberty, treatment of benign prostatic hyperplasia, palliative treatment or remission of hormonal-dependent tumors of the prostate, the treatment of cryptorchidism, hirsutism in women, gastric motility disorders, dysmenorrhea, and endometriosis.

Current LHRH antagonists are decapeptides which, because of their low oral bioavailability, are administered either intravenously or subcutaneously. Non-peptide heterocyclic antagonists have been reported in the literature, see for example, WO 95/280405, WO 95/29900, WO 97/22707, WO 97/21704 and WO 97/2103. Non-peptide LHRH antagonists have the possible advantage of improved oral bioavailability and are smaller molecules.

However, there are no known reports of macrolide compounds as LHRH antagonists in the literature. Macrolide antibiotics and macrolide prokinetic agents are known. For example, macrolide antibiotics derived from erythromycin which contain 11,12-cyclic carbamate moieties are disclosed in EP 248 279 A2. The 3'-N substituted erythromycin derivatives, which are effective antibacterial agents are described in EP 0 559 896 A1. Macrocyclic lactone (macrolide) prokinetic agents are known. See J. S. Gidda et al, in European Patent Application No. 0349100, published Jan. 3, 1990, which discloses 12-membered macrolides for use as gastrointestinal motility enhancers. S. Omura and Z. Itoh, in U.S. Pat. No. 4,677,097, issued Jun. 30, 1987; European Application No. 215,355, published Mar. 25, 1987; and European Application No. 213,617, published Mar. 11, 1987; disclose derivatives of erythromycins A, B, C and D which are useful as stimulants of digestive tract contractile motion. Additionally, T. Sunazuka, et al., *Chem. Pharm. Bull.* 37(10): 2701–2709 (1989) discloses quaternary derivatives of 8,9-anhydroerythromycin A 6,9-hemiacetal and 9,9-dihydro-erythromycin A 6,9-epoxide with gastrointestinal motor stimulating activity.

None of these references disclose novel 3',3'-N-bis-desmethyl-3',3'-N-bis-substituted-6-O-methyl-11-deoxy-11,12-cyclic carbamate erythromycin A derivatives of the present invention, which are effective as LHRH antagonists.

3'-N-desmethyl-3'-N-monosubstituted-6-O-methyl-11-deoxy-11,12-cyclic carbamate erythromycin A derivatives are disclosed in the commnonly owned U.S. Application filed concurrently herewith. The 3',3'-N-bis-desmethyl-3',3'-N-bis-substituted-6-O-methyl-11-deoxy-11,12-cyclic carbamate erythromycin A derivatives of the present invention are disclosed herewith.

SUMMARY OF THE INVENTION

In one aspect, the present invention relates to a compound having the formula:

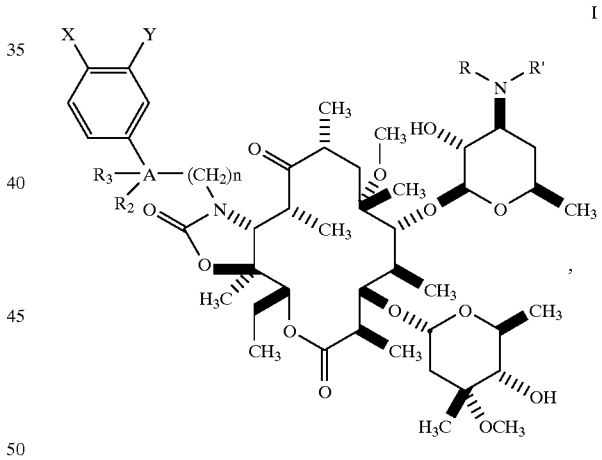

or a pharmaceutically acceptable salt or ester thereof, wherein

A is selected from the group consisting of:
(a) —C,
(b) —N, and
(c) —O;

X and Y are independently at each occurrence selected from the group consisting of:
(a) hydrogen,
(b) halide,
(c) trifluoromethyl,
(d) alkoxy,
(e) alkyl,
(f) aryl, and
(g) substituted aryl;

R and R' are selected from the group consisting of:
(a) alkyl,
(b) cycloalkyl,
(c) heterocylic,
(d) substituted heterocyclic,
(e) alkylcycloalkyl,
(f) substituted alkylcycloalkyl,
(g) alkylaryl,
(f) alkylheterocyclic,
(g) alkenyl,
(h) alkynyl,
(i) —C(S)—NHR$_4$, C(NR$_4$)—NHR$_4$, wherein R$_4$ is hydrogen, alkyl, or aryl; and
(j) —(CH$_2$)n—C(CH$_2$)m—R$_5$, wherein m is 2, 3, 4, or 5, and R$_5$ is alkyl, alkoxy, aryl, or substituted aryl;
R$_2$ and R$_3$ are independently at each occurrence
(a) hydrogen,
(b) methyl, or
R$_2$ and R$_3$ together form a cyclic moiety, when A is C;
R$_3$ is absent when A is N; and
n=1, 2or3.

In another aspect, the present invention relates to a process for preparing the compound formula I. The process comprises the steps of:
(a) reacting a compound of formula:

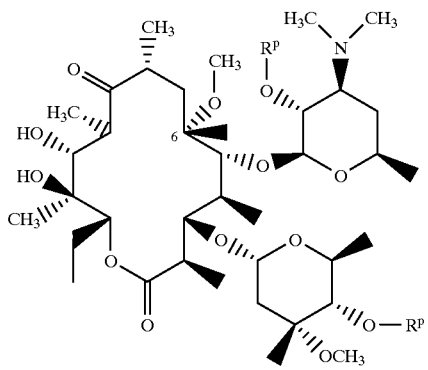

with sodium hexamethyldisilazide and carbonyldiimidazole to afford a compound of the formula:

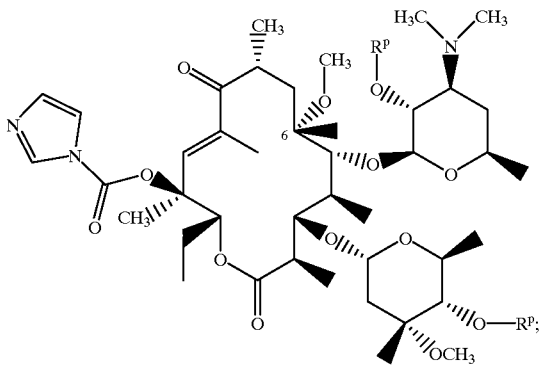

(b) reacting the compound obtained in step (a) with a compound an amino compound of the formula:

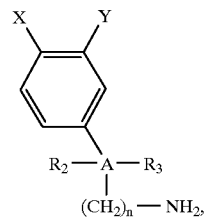

followed by deprotection of the 2',4"-protected hydroxy groups to afford a compound of the formula:

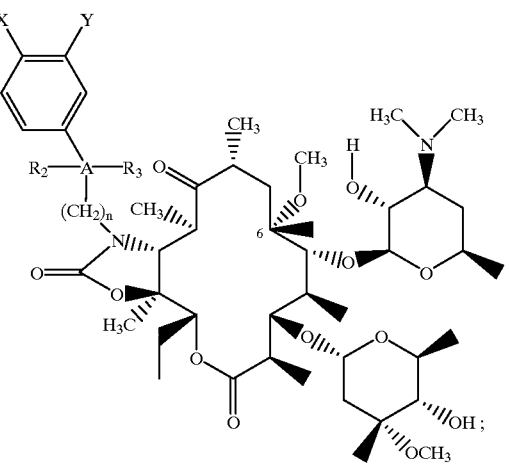

(c) stepwise desmethylating the 3'-amino by treating the compound obtained in step (b) with iodine in the presence of a base to afford a compound of the formula:

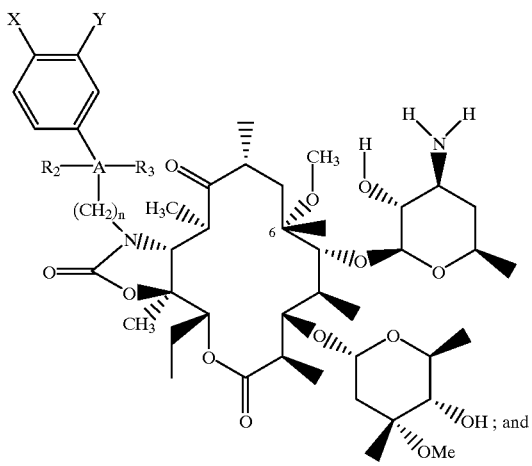

(d) alkylating the 3',3'-N-bisdesmethylated compound obtained in step (c) with an alkylating agent In another embodiment of the process, the process comprises the steps of:
(c) selectively desmethylating the compound obtained in step (b) to obtain the compound of the formula:

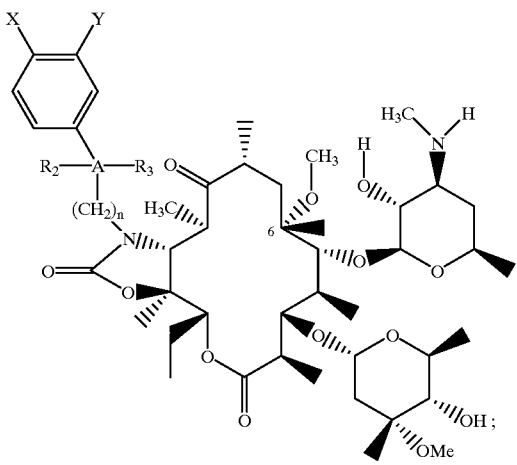

(d) alkylating the 3'-N-desmethylated compound obtained in step (c) with an alkylating agent to afford a compound of the formula:

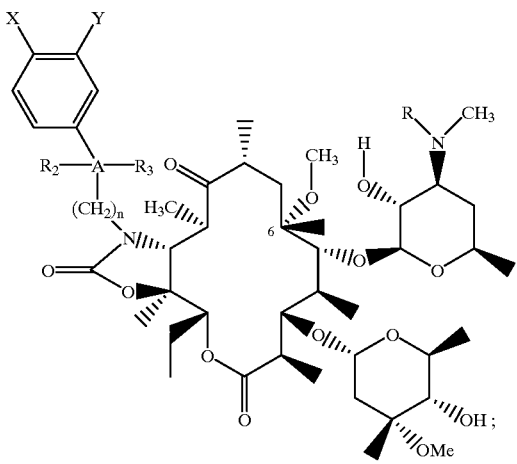

(e) desmethylating the 3'-amino by treating the compound obtained in step (d) with iodine in the presence of a base to afford a compound of the formula:

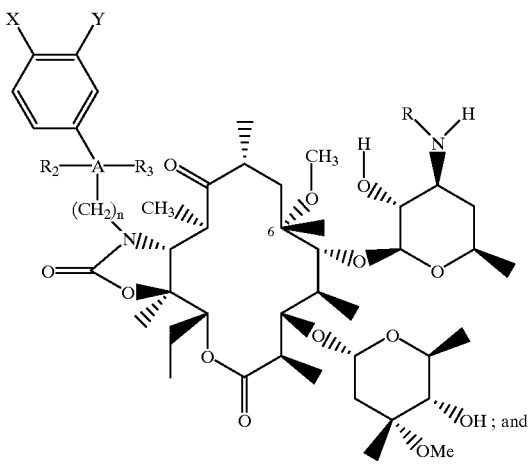

(f) alkylating the 3'-N-desmethylated compound obtained in step (e) with an alkylating agent.

The compounds of the invention exhibit little or no antibacterial activity, but they bind to the LHRH receptors and are effective LHRH antagonists. Thus, these compounds are effective in the treatment of prostate cancer, endometriosis, precocious puberty and other types of diseases which are related to sex hormones.

Accordingly, in another aspect of the invention, the present invention relates to pharmaceutical compositions which are useful as LHRH antagonists and suppress LH, testosterone, estradiol and estrogen in mammals.

In still another aspect, the present invention relates to a method of suppressing levels of sex hormones in male or female mammals comprising administering to a host in need of such treatment a therapeutically effective amount of a LHRH compound in combination with a therapeutically effective amount of an antiandrogenic agent.

DETAILED DESCRIPTION OF THE INVENTION

The terms "loweralkyl" or "alkyl" as used herein refer to straight or branched chain alkyl radicals containing from 1 to 20 carbon atoms, sometimes represented as Cx-Cy-alkyl where x and y respectively represent the minimum and maximum number of carbon atoms in the alkyl radical. Examples of loweralkyl include, but are not limited to, methyl, ethyl, n-propyl, isopropyl, n-butyl, isobutyl, sec-butyl, t-butyl, n-pentyl, 1-methylbutyl, 2,2-dimmethylpentyl, 2,2-dimethylpropyl, n-hexyl and the like.

The term "alkoxy" or "lower alkoxy" as used herein refers to a loweralkyl group, as defined above, which is bonded to an oxygen atom in an ether linkage. Examples of alkoxy include, but are not limited to, methoxy, ethoxy, isopropoxy, n-pentyloxy, t-butoxy, n-octyloxy and the like. This alkoxy radical can also contain a ring which include, but are not limited to, five or six atom ring composed of carbons, one or two heteroatoms such as nitrogen, oxygen.

The term "alkenyl" as used herein refers to a branched or straight hydrocarbon chain comprising two to twenty carbon atoms, preferably four to twelve carbon atoms, especially about eight to ten carbon atoms, which also comprises one or more carbon-carbon double bonds, preferably about one to three double bonds. Compounds of the invention may either have a known configuration or may exist as a mixture of isomers.

The term "alkynyl" as used herein refers to a branched or straight hydrocarbon chain comprising two to twenty carbon atoms, preferably four to twelve carbon atoms, especially about eight to ten carbon atoms, which also comprises one or more carbon-carbon triple bonds, preferably about one triple bond. Compounds of the invention may either have a known configuration or may exist as a mixture of isomers.

The term "cycloalkyl" as used herein refers to saturated monocyclic hydrocarbon groups having from three to seven carbon atoms in the ring, including, but not limited to, cyclopropyl, cyclobutyl cyclopentyl, cyclohexyl, cycloheptyl and the like. The cyclic group may be optionally substituted with, for example, lower alkyl, hydroxy, halogen or an amino.

The term "alkylcycloalkyl" as used herein refers to a cycloalkyl group as defined above, appended to a loweralkyl radical. The alkylcycloalkyl group is attached to the parent moiety through the alkyl radical wherein the alkyl radical is of one to six carbon atoms. Examples include, but are not limited to, cyclopropylmethyl, cyclopropylethyl, cyclobutyl-methyl and the like.

The term "aryl" as used herein refers to a mono-, fused bicyclic or fused tricyclic carbocyclic ring system having one or more aromatic rings including, but not limited to, phenyl, naphthyl, tetrahydronaphthyl, phenanthrenyl, biphenylenyl, indanyl, indenyl and the like.

The term "substituted aryl" as used herein refers to an aryl group as defined herein substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, methoxymethoxy, amino, $C_1$–$C_3$-alkyl-amino, di($C_1$–$C_3$-alkyl-) amino, formyl, carboxy, alkoxycarbonyl, $C_1$–$C_3$-alkyl-CO—O—, $C_1$–$C_3$-alkyl-CO—NH—, or carboxamide; except that tetrafluorophenyl and pentafluorophenyl are also included within the definition of "substituted aryl".

The term "arylalkyl" as used herein refers to an aryl group as defined above appended to an alkyl group defined above. The arylalkyl group is attached to the parent moiety through an alkyl group wherein the alkyl group is one to six carbon atoms. The aryl group in the arylalkyl group may be substituted as defined above. Examples include, but are not limited to, 3-(4-hydroxyphenyl)propyl, 1-methyl-3-(4-hydroxyphenyl)-propyl, 4-hydroxybenzyl, and the like.

The terms "heterocyclic ring" or "heterocyclic" or "heterocycle" as used herein refers to any 3- or 4-membered ring containing a heteroatom selected from oxygen, nitrogen and sulfur; or a 5-, 6- or 7-membered ring containing one, two or three nitrogen atoms; one nitrogen and one sulfur atom; or one nitrogen and one oxygen atom. The 5-membered ring has 0–2 double bonds and the 6- and 7-membered ring have 0–3 double bonds. The nitrogen heteroatoms can be optionally quaternized. The term "heterocyclic" also includes bicyclic groups in which any of the above heterocyclic rings is fused to a benzene ring or a cyclohexane ring or another heterocyclic ring (for example, indolyl, quinolyl, isoquinolyl, tetrahydroquinolyl, and the like). Heterocyclics include: azetidinyl, benzimidazolyl, 1,4-benzodioxanyl, 1,3-benzodioxolyl, benzoxazolyl, benzothiazolyl, benzothienyl, dihydroimidazolyl, dihydropyranyl, dihydrofuranyl, dioxanyl, dioxolanyl, furyl, homopiperidinyl, imidazolyl, imidazolinyl, imidazolidinyl, indolinyl, indolyl, isoquinolinyl, isothiazolidinyl, isothiazolyl, isoxazolidinyl, isoxazolyl, morpholinyl, naphthyridinyl, oxazolidinyl, oxazolyl, piperaziriyl, piperidinyl, pyrazinyl, pyrazolinyl, pyridyl, pyrimidinyl, pyrrolidinyl, pyrrolinyl, pyrrolyl, quinolinyl, tetrahydrofuranyl, tetrahydropyranyl, thiazolidinyl, thiazolyl, and thienyl.

Heterocyclics can be unsubstituted or monosubstituted or disubstituted with substituents independently selected from hydroxy, halo, oxo (=O), alkylimino (R*N= wherein R* is a loweralkyl group), cycloalkyl, aryl, arylalkyl, and loweralkyl. In addition, nitrogen containing heterocycles can be N-protected.

The term "(heterocyclic)alkyl" as used herein refers to a heterocyclic group as defined above appended to a loweralkyl radical as defined above. The (heterocylic)alkyl group is attached to the parent moiety through an alkyl group wherein the alkyl group is of one to six carbon atoms. Examples include, but are not limited to, 2-pyridylmethyl, 4-pyridylmethyl, 2-pyridylethyl, 3-(3-pyridyl)propyl, 3-(2-pyridyl)propyl, 3-(4-pyridyl)propyl, 2-furylmethyl and the like.

The term "substituted (heterocyclic)alkyl" as used herein, refers to a heterocycloalkyl group, as defined above, wherein the heterocyclic group or the alkylgroup is substituted by independent replacement of one, two or three of the hydrogen atoms thereon with Cl, Br, F, I, OH, cyano, mercapto, nitro, $C_1$–$C_3$-alkyl, halo-$C_1$–$C_3$-alkyl, $C_1$–$C_6$-alkoxy, thio-$C_1$–$C_6$-alkoxy, hydroxyalkyl, methoxymethoxy, amino, $C_1$–$C_3$-alkyl-amino, di($C_1$–$C_3$-alkyl)amino, carboxaldehydo, carboxy, alkoxycarbonyl, $C_1$–$C_3$-alkyl-CO—O—, $C_1$–$C_3$-alkyl-CO—NH—, or carboxamide.

Examples include, but are not limited to, 3-[(5-methyl)-2-pyridyl]propyl, 3-[(6-methyl)-2-pyridyl]propyl, 4-[(6-methyl)-2-pyridyl]butyl, (5-nitro)-2-thienylmethyl and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isoxazolyl, thiadiazolyl, oxadiazolyl, thienyl, furanyl, quinolinyl, isoquinolinyl, and the like.

The term "substituted heteroaryl" as used herein refers to a heteroaryl group as defined herein substituted by independent replacement of one, two or three of the hydrogen atoms thereon with Cl, Br, F, I, OH, $C_1$–$C_3$-aLkyl, $C_1$–$C_6$-alkoxy, methoxymethoxy, amino, or $C_1$–$C_3$-alkyl-amino, or may also refer to a mono-oxo substituted heteroaryl compound, such as 4-oxo- 1H-quinoline, for example.

The term "aprotic solvent" as used herein refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, ethers such as diethyl ether and bis-methoxymethyl ether, as well as various other compounds like dimethyl formamide, acetonitrile, acetone and ethyl acetate. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick, et al., Vol. II, in the Techniques of Chemistry Series, John Wiley & Sons, N.Y., 1986.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the final isolation and purification of the compounds of the invention, or separately by reacting the free base function with a suitable organic or inorganic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tarric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable esters" refer to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which, each alkyl or alkenyl moiety advantageously has not more than 6 carbon atoms. Examples of particular esters incude formates, acetates, propionates, butyrates, acrylates, and ethyl succinates.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

PREFERRED EMBODIMENTS

The preferred compounds of the invention comprise those in which R and R' are alkyl, alkenyl, cycloalkyl, heterocyclic, (heterocyclic)alkyl or alkylcycloalkyl; X and Y are independently chloro, fluoro, dioxalano, hydrogen, or alkoxy; A is —C; $R_2$ and $R_3$ are hydrogen or cyclopropyl and n is 1.

Representative compounds of the invention are selected from the group consisting of:

3',3'-N-bisdesmethyl-3',3'-N-biscyclopropylmethyl-11-deoxy-11-[carboxy-(3,4-dichlorophenethylamino)]-6-O-methyl-erythromycin A 11,12-(cyclic carbamate);

3',3'-N-bisdesmethyl-3',3'-N-biscyclobutyl-11-deoxy-11-[carboxy-(3,4-dichlorophenethylamino)]-6-O-methyl-eryhomycin A 11,12-(cyclic carbamate);

3',3'-N-bisdesmethyl-3',3'--N-biscyclopropylmethyl 11-deoxy-11-[carboxy-(4-chlorophenethylamino)]-6-O-methyl-erythromycin A 11,12-(cyclic carbamate);

3',3'-N-bisdesmethyl-3',3'-N-biscyclobutyl-11-deoxy-11-[carboxy-(4-chlorophenethylamino)]-6-O-methyl-erythromycin A 11,12-(cyclic carbamate);

3',3'-N-bisdesmethyl-3'-N-cyclobutyl-3'-N-isopropyl-11-deoxy-11-[carboxy-(4-chlorophenethylamino)]-6-O-methyl-erythromycin A 11,12-(cyclic carbamate);

3,3'-N-bisdesmethyl-3'-N-isopropyl-3'-N-propyl-11-deoxy-11-[carboxy-(4-chlorophenethylamino)]-6-O-methyl-erythromycin A 11,12-(cyclic carbamate);

3',3'-N-bisdesmethyl-3'-N-cyclopropylmethyl-3'-N-isopropyl-11-deoxy-11-[carboxy-(4-chlorophenethylamino)]-6-O-methyl-erythromycin A 11,12-(cyclic carbamate);

3',3'-N-bisdesmethyl-3'-N-ethyl-3'-N-isopropyl-11-deoxy-11-[carboxy-(4-chlorophenethylamino)]-6-methyl-erythromycin A 11,12-(cyclic carbamate);

3',3-N-bisdesmethyl-3'-N-cyclobutylmethyl-3'-N-cyclopropylmethyl-11-deoxy-11-[carboxy-(4-chlorophenethylamino)]-6-O-methyl-erythromycin A 11,12-(cyclic carbamate);

3',3'-N-bisdesmethyl-3',3'-N-biscyclopropylmethyl-11-deoxy-11-[carboxy-(4-methoxyphenethylamino)]-6-O-methyl-erythromycin A 11,12-(cyclic carbamate);

3',3'-N-bisdesmethyl-3',3'-N-biscyclopropylmethyl-11-deoxy-11-[carboxy-(4-fluorophenethylamino)]-6-O-methyl-erythromycin A 11,12-(cyclic carbamate);

3',3'-N-bisdesmethyl-3',3'-N-biscyclobutyl-11-deoxy-11-[carboxy-(4-chloro-3-fluorophenethylamnno)]-O-methyl-erythromycin A 11,12-(cyclic carbamate);

3',3'-N-bisdesmethyl-3',3'-N-biscyclopropylmethyl-11-deoxy-11-[carboxy-(4-chloro-3-fluorophenethylamino)]-6-O-methyl-erythromycin A 11,12-(cyclic carbamate);

3',3'-N-bisdesmethyl-3',3'-N-biscyclobutyl-11-deoxy-11-[carboxy-(3-chloro-4-fluorophenethylamino)]-O-methyl-erythromycin A 11,12-(cyclic carbamate);

3',3'-N-bisdesmethyl-3',3'-N-biscyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopentyl-3'-N-cyclopropylmethyl-11-deoxy-11-[carboxy-(3-chloro-4-difluorophenethylamino)]-6-O-methyl-erythromycin A 11,12-(cyclic carbamate);

3',3'-N-bisdesmethyl-3',3'-N-biscyclopropylmethyl-11-deoxy-11-[carboxy-(3,4-difluorophenethylamino)]-6-O-methyl-erythromycin A 11,12-(cyclic carbamate);

3',3'-N-bisdesmethyl-3',3'-N-biscyclobutyl-11-deoxy-11-[carboxy-(3,4-difluorophenethylamino)]-6-O-methyl-erythromycin A 11,12-(cyclic carbamate);

3',3'-N-bisdesmethyl-3'-N-cyclobutyl-3'-N-cyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3',3'-N-bis[3-(3-pyridyl)propyl]-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(4-hydroxymethyl-2-furyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-3-(4-pyridyl)propyl-11-deoxy-11-[carboxy-(3-chloro-4-fluorophenethylamino)]6-O-methyl-erythromycin A 11,12-(cyclic carbamate);

3',3'-N-bisdesmethyl-3'-N-cyclopropylmethyl-3'-N-4-(hydroxymethyl-2-furyl) methyl-11-deoxy-11-[carboxy-(3-chloro-4fluorophenethylamino)]-6-O-methyl-erythromycin A 11,12-(cyclic carbamate);

3',3'-N-bisdesmethyl-3'-N-cyclopropylmethyl-3'-N-(2-furyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-[6-methyl-(2-pyridyl)]methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-bis-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-bis-(1-methylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-(1-methylcyclopropyl)methyl-3'-N-cyclopropylmethyl-11-deoxy-11-[carboxy-(3-chloro- 4-fluorophenethylamino)]-6-O-methyl-erythromycin A 11,12-(cyclic carbamate);

3',3'-N-bisdesmethyl-3'-N-(1-methylcyclopropyl)methyl-3'-N-cyclopropylmethyl-11-deoxy-11-[carboxy-(3,4-dichlorophenethylamino)]-6-O-methyl-erythromycin A 11,12-(cyclic carbamate);

3',3'-N-bisdesmethyl-3'-N-isopropyl-3'-N-cyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isopropyl-3'-N-cyclopropylmethyl-11-deoxy-11-[carboxy-(3,4-dichlorophenethylamino)]-6-O-methyl-erythromycin A 11,12-(cyclic carbamate);

3',3'-N-bisdesmethyl-3'-N-isopropyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isopropyl-3'-N-(1-methylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(biscyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(biscyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(2,2-dimethylpropyl)-11-deoxy-11-[carboxy-(3-chloro-4fluorophenethylamino)]-6-O-methyl-erythromycin A 11,12-(cyclic carbamate);

3',3'-N-bisdesmethyl-3'-N-cyclopropylmethyl-3'-N-(2,2-dimethylpropyl)-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-[3-(4-hydroxy-3-methoxyphenyl)-1-methyl]propyl-11-deoxy-11-[carboxy-(3-chloro4-fluorophenethylamino)]-6-O-methyl-erythromycin A 11,12-(cyclic carbamate);

3',3'-N-bisdesmethyl-3'-N-cyclopropylmethyl-3'-N-[3-(4-hydroxy-3-methoxyphenyl)-1-methyl]propyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclobutyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclobutyl-3'-N-(1-methylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-cyclopropylmethyl-3'-N-(1-ethylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-ethylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-phenylcyclopropyl)methyl-11-deoxy-11-[carboxy-(3-chloro-4-fluorophenethylamiino)]-6-O-methyl-erythromycin A 11,12-(cyclic carbamate);

3',3'-N-bisdesmethyl-3'-N-cyclopropylmethyl-3'-N-(1-phenylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-ethyl-3'-N-(11-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-ethyl-3'-N-(1-methylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-isobutyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isobutyl-3'-N-(1-methylcyclopropyl)methyl-11-deoxy-11-[carboxy-(3,4dichlorophenethylamino)]-6-O-methyl-erythromycin A 11,12-(cyclic carbarnate);

3',3'-N-bisdesmethyl-3'-N-cyclopropylmethyl-3'-N-(1-allylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-allylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-benzylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-benzylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-bis-(1-methylcyclobutyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-bis-(1-methylcyclobutyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-methylcyclobutyl)methyl-11-deoxy-11-[carboxy-(3-chloro-4-fluorophenethylamino)]-6-O-methyl-erythromycin A 11,12-(cyclic carbamate); and 3',3'-N-bisdesmethyl-3'-N-cyclopropylmethyl-3'-N-(1-methylcyclobutyl)methyl-11-deoxy-11-[carboxy-(3,4-dichlorophenethylamino)]-6-O-methyl-erythromycin A 11,12-(cyclic carbamate).

The more preferred compounds of the invention are:

3',3'-N-bisdesmethyl-3'-N-biscyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-biscyclobutyl-11-deoxy-11-[carboxy-(3-chloro-4-fluorophenethylamino)]-6-O-methyl-erythromycin A 11,12-(cyclic carbamate).

3',3'-N-bisdesmethyl-3',3'-N-bis-(1-methylcyclopropyl)methyl-11-deoxy-11-[carboxy-(3, chloro-4-fluorophenethylamino)]-6-O-methyl-erythromycin A 11,12-(cyclic carbamate); and 3',3'-N-bisdesmethyl-3'-N-isopropyl-3'-N-(1-methylcyclopropyl)methyl-11-deoxy-11-[carboxy-(3-chloro-4fluorophenethylamino)]-6-O-methyl-erythromycin A 11,12-(cyclic carbamate).

EFFECT AND UTILITIES OF LHRH AGONISTS AND ANTAGONISTS

The LHRH agonist and antagonist compounds of the invention are useful for treatment of precocious puberty, prostate cancer, benign prostatic hyperplasia (BPH), endometriosis, uterine fibroids, breast cancer, acne, premenstrual syndrome, polycystic ovary syndrome and diseases which result from excesses or deficiencies in gonadal hormone production in either sex of humans and animals. The LHRH antagonists of the invention are also useful for controlling reproduction in both female and males. Compounds of the invention are useful for suppressing levels of testosterone and dihydrotestosterone (DHT) in male and estrogen and estradiol in female.

In the practice of the method of this invention an effective amount of a compound of the invention or a pharmaceutical composition containing the same is administered to the human or animal in need of, or desiring, such treatment. These compound or compositions may be administered by any variety of routes depending upon the specific end use, including orally, parenterally (including subcutaneous, intramuscular and intravenous administration), vaginally (particularly for contraception), rectally, buccally (including sublingually), transdermally or intranasally. The most suitable route in any given case will depend upon the use, particular active ingredient, the subject involved, and the judgment of the medical practitioner. The compound or composition may also be administered by means of slow-release, depot or implant formulations as described more fully herein below.

In general, to modulate levels of sex hormones in male or female mammals for the uses herein above described, it is expedient to administer the active ingredient in amounts between about 1 and 200 mg/kg body weight per day, preferably between 1 and 30 mg/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of afflication or need and the judgment of the medical practitioner. In general, parenteral administration requires lower dosage than other methods of administration which are more dependent upon absorption.

A further aspect of the present invention relates to pharmaceutical compositions comprising the compound of the invention as an active ingredient in admixture with a pharmaceutically acceptable, non-toxic carrier. As mentioned above, such compositions may be prepared for use for parenteral (subcutaneous, intramuscular or intravenous) administration, particularly in the form of liquid solutions or suspensions; for use in vaginal or rectal administration, particularly in semisolid forms such as creams and suppositories; for oral or buccal administration, particularly in the form of tablets or capsules, or intranasally, particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for inhalation administration may be solid and contain as excipients, for example, lactose, or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of a compound of the invention which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutarnic acid, naphthalene mono- or di-sulfonic acids, polygalacturonic acid, and the like; (b) a salt with a poly valent metal cation such as zinc, calcium, bismuth, barium, magnesium, aluminum, copper, cobalt, nickel, cadmium and the like, or with an organic cation formed from e.g., N,N'-debenzylethylenediamine or ethylenediamine; or (c) combinations of (a) and (b) e.g., a zinc tannate salt. Additionally, the compounds of the present invention or preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as polylactic acid/polyglycolic acid polymer for example as described in U.S. Pat. No. 3,773,919. The compounds of the invention or, preferably, relatively insoluble salts such as those described above may also be formulated in cholesterol matrix pellets, particularly for use in animals. Additional slow release, depot or implant formulations, e.g. liposomes, are well known in the literature. See, for example, Sustained and Controlled Release Drug Delivery Systems, J. R. Robinson ed., Marcel Dekker, Inc., New York, 1978. Particular reference with respect to LHRH type compounds may be found, for example, in U.S. Pat. No. 4,010,125.

LHRH ANTAGONIST ACTIVITY

Representative compounds of the present invention were evaluated in in vitro tests for LHRH rat pituitary receptor binding (pKI) and for LH inhibition from rat pituitary cells for antagonist potency (pA2). The tests employed the methods detailed in F. Haviv, et al. *J. Med. Chem.*, 2340–2344 (1989). The receptor binding affinity ($pK_I$) is the negative equilibrium dissociation constants. The results of the $pK_I$ for representative his invention are presented in Table 1.

TABLE 1

| Example | $pK_I$ | Example | $pK_I$ |
|---------|--------|---------|--------|
| 1       | 7.73   | 14      | 9.60   |
| 2       | 8.50   | 15      | 8.90   |
| 3       | 8.38   | 16      | 8.87   |
| 4       | 8.62   | 17      | 8.50   |
| 5       | 9.08   | 18      | 9.40   |
| 6       | 8.08   | 19      | 9.08   |
| 7       | 8.56   | 20      | 8.40   |
| 8       | 8.60   | 21      | 8.34   |
| 9       | 8.20   | 22      | 8.72   |
| 10      | 8.85   | 23      | 8.98   |
| 11      | 8.66   | 24      | 8.00   |
| 12      | 9.00   | 25      | 8.58   |
| 13      | 8.94   |         |        |

The $pA_2$ value is the negative logarithm of the concentration of antagonist which shifts the response curve produced by the agonist leuprolide to two-fold higher concentration. Leuprolide is the LHRH agonist having the structure pyro-Glu$^1$-His$^2$-Trp$^3$-Ser$^4$-Tyr$^5$-D-Leu$^6$-Leu$^7$-Arg$^8$-Pro$^9$-NHEt and is disclosed and claimed in U.S. Pat. No. 4,005,063. Typically $pA_2$ values of 7.0 or greater are indicative of good LHRH antagonist potency. The $pA_2$ values for representative compounds are set forth in Table 2 below.

TABLE 2

| Example | pA$_2$ |
|---------|--------|
| 2 | 8.27 |
| 5 | 9.08 |
| 4 | 9.90 |
| 13 | 9.53 |
| 14 | 9.12 |
| 17 | 8.81 |
| 18 | 8.34 |

SYNTHETIC METHODS

The compounds and processes of the present invention will be better understood in connection with the following synthetic Schemes 1–6 which illustrate the methods by which the compounds of the invention may be prepared. The compounds are prepared by utilizing commercially available or synthesized reagents.

ABBREVIATIONS

Abbreviations which have been used in the descriptions of the scheme and the examples that follow are: Ac for acetyl; APCI for atmospheric pressure chemical ionization; CDI for carbonyldiimidazole; CH$_3$CN for acetonitrile; CI or DCI for desorption chemical ionization; DMF for dimethyl formamide; ESI for electrospray ionization; EtOAc for ethyl acetate; FAB for fast atom bombardment; FTIR for Fourier transform infrared spectroscopy; HPLC for high performance liquid chromatography; IR for infrared spectroscopy; MeOH for methanol; MHz for megahertz; MIC for microscope; MS for mass spectra; NaHMDS for sodium hexamethyldisilazide; NMR for nuclear magnetic resonance; R$_f$ for retention factor; R$_t$ for retention time; TBAF for tetrabutylammonium fluoride; THF for tetrahydrofuran; TLC for thin layer chromatography; TMS for trimethylsilyl; TMSCI for trimethylsilyl chloride; and DCM for dichloromethane.

The starting material 6-O-methyl-erythromycin A 1 (clarithromycin, commercially available as BIAXIN® from Abbott Laboratories) is protected at the 2' and 4" positions by reaction with a suitable hydroxy protecting reagent, such as described by T. W. Greene and P. G. M. Wuts in *Protective Groups in Organic Synthesis*, 2nd. ed., John Wiley & Son, Inc. 1991. Hydroxy protecting reagents include, for example, acetic anhydride, benzoic anhydride, benzylchloroformate, hexamethyldisilazane, or trialkylsilyl chloride in an aprotic solvent.

Scheme 1

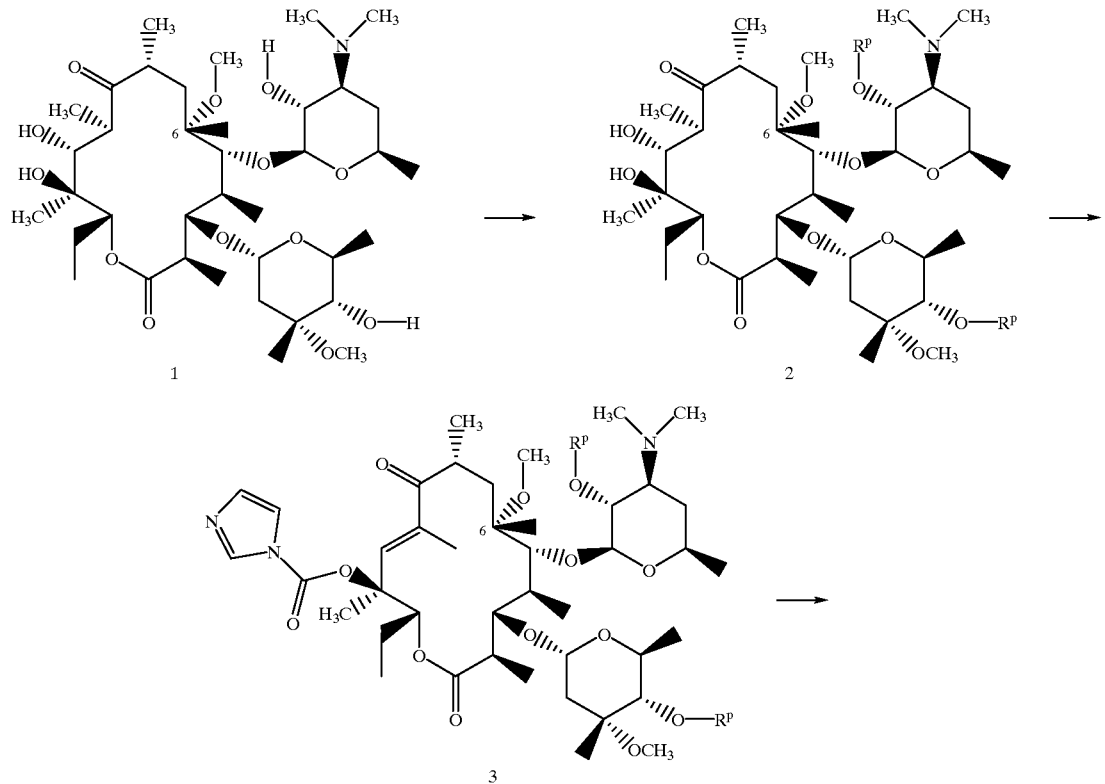

-continued
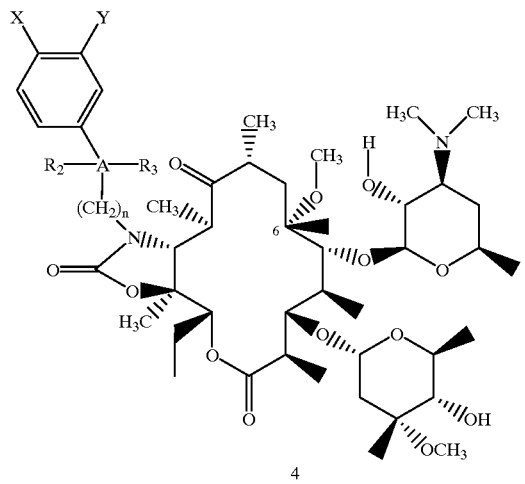
4
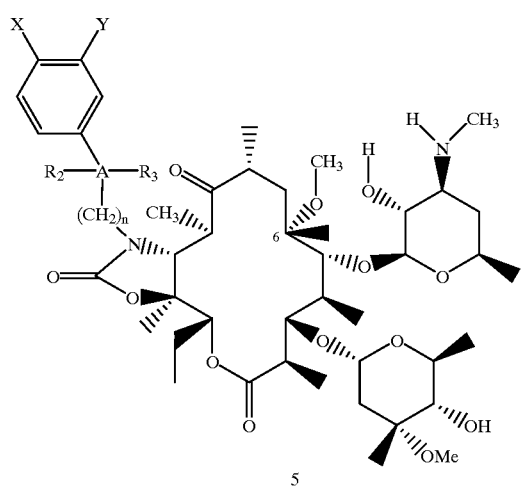
5
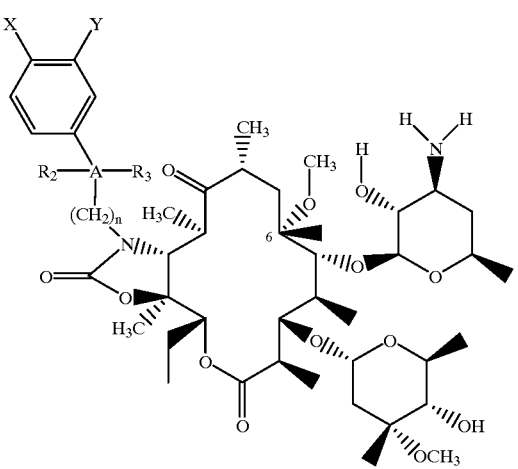
6
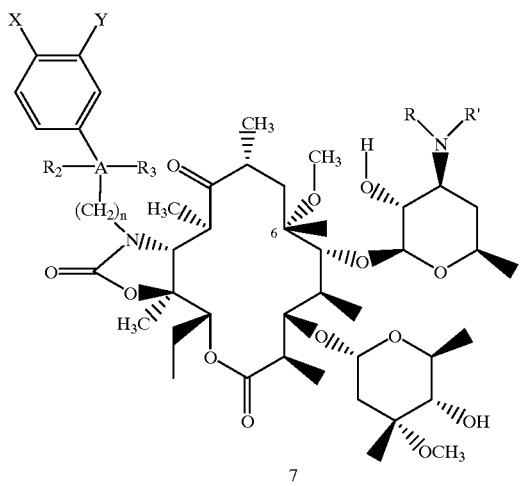
7

Protection of 2'- and 4"-hydroxy groups of 6-O-methylerythromycin A 1 as shown in Scheme 1 may be accomplished sequentially or simultaneously to provide compound 2 where Rp is a hydroxy protecting group. A preferred protecting group Rp is trimethylsilyl or acetyl.

Examples of aprotic solvents are dichloromethane, chloroform, DMF, tetrahydrofuran (THF), N-methyl pyrrolidinone, dimethylsulfoxide, diethylsulfonate, N,N-dimethylformamide, N,N-dimethylacetamide, hexamethylphosphoric triamide, a mixture thereof or a mixture of one of these solvents with ether, tetrahydrofuran, 1,2-dimethoxyethane, acetonitrile, ethyl acetate, acetone and the like. Aprotic solvents do not adversely affect the reaction, and are preferably dichloromethane, chloroform, DMF, tetrahydrofuran (THF), N-methyl pyrrolidinone or a mixture thereof.

The protected compound 2 is treated with sodium hexamethyldisilazide or sodium hydride in an aprotic solvent at 0 to 25° C. and carbonyldiimidazole to yield compound 3. Treatment of compound 3 with an amino compound of the formula

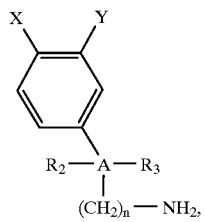

either without solvent or in acetonitrile at 25 to 80° C., followed by deprotection results in formation of N-substituted cyclic carbamate represented by compound 4. Deprotection of the 2'- and 4"-hydroxy protecting groups carried out by the methods described by T. W. Greene and P. G. M. Wuts in *Protective Groups in Organic Synthesis*, 2nd. ed., John Wiley & Son, Inc. 1991.

In one embodiment of the process, the desmethylation of the 3'-N-dimethyl group is carried out stepwise by treating compound 4 with iodine in the presence of a suitable base, such as sodium acetate and a light or a heat source, followed by quench with sodium thiosulfate and work up to remove the first methyl group to afford compound 5. The second methyl group is removed by treatment with iodine, a moderate base such as tribasic potassium phosphate and a light source to form the bisdesmethyl amine 6. N-Desmethylation can also be accomplished by reaction of compound 4 with chloroformate reagents such as benzyl chloroformate, allyl chloroformate, vinyl chloroformate and the like.

Alkylation of 3'-N-bisdesmethyl compound 6 is achieved by reaction with an appropriate aldehyde or ketone in the presence of a hydride metal such as sodium cyanoborohydride or sodium triacetoxyborohydride or in the presence of Pd/C catalyst in a protic or non-protic solvent under hydrogen atmosphere. The aldehydes and ketones that may be used in preparing compound 7 include, for example, cyclopropyl carboxaldehyde, acetone, n-propanal, cyclohexanone, cyclopentanone, isovaleraldehyde, cyclobutanone, isopropylaldehyde, 2-pyridinecarboxaldehyde, 4-thiazolecarboxaldehyde.

Alkylation of 3',3'-N-bisdesmethyl compound 6 can also be achieved by the reaction with an appropriate alkylating agent in the presence of a base by the methods known in the art to afford compound 7. The alkylating agents which may be used in preparing compound 7 include loweralkyl halides such as ethyl bromide, halo-substituted loweralkyl halides, cyano-substituted loweralkyl halides, hydroxy-substituted loweralkyl halides, other loweralkenyl halides such as methylallyl chloride, loweralkynyl halides such as propargyl bromide, lower cycloalkyl halides, lower cycloalkylmethyl halides such as lower cyclopropylmethyl and benzyl halides.

In another embodiment of the process, both the desmethylation and the alkylation are carried out sequentially as illustrated in Scheme 2. The first desmethylation of the compound 4 is carried out as described above to obtain the compound 5, which is then monoalkylated in the manner described above to yield 8. The second demethylation is then accomplished as described above to yield compound 9, which is then alkylated to afford the compound 7.

Scheme 2

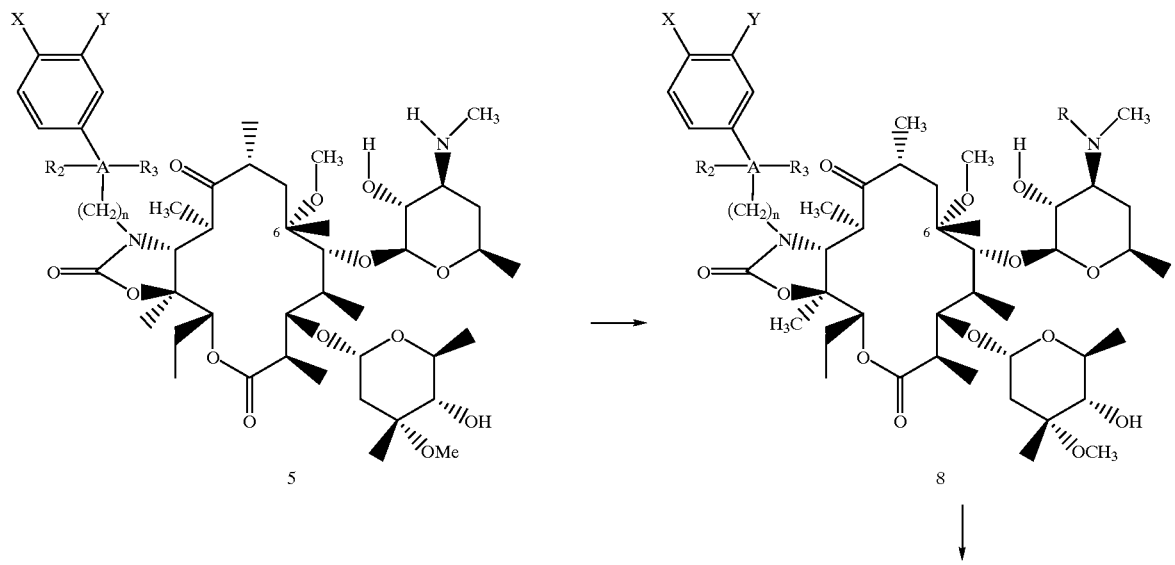

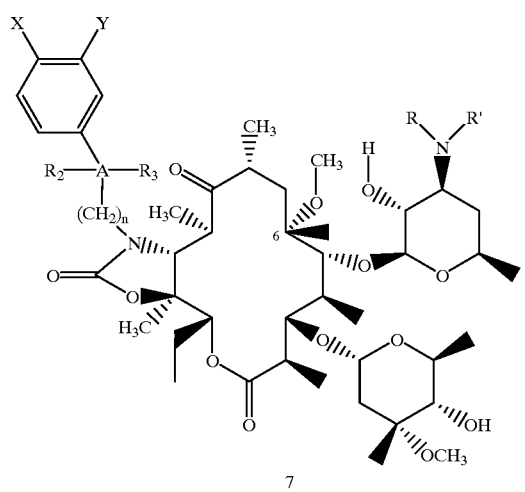

7

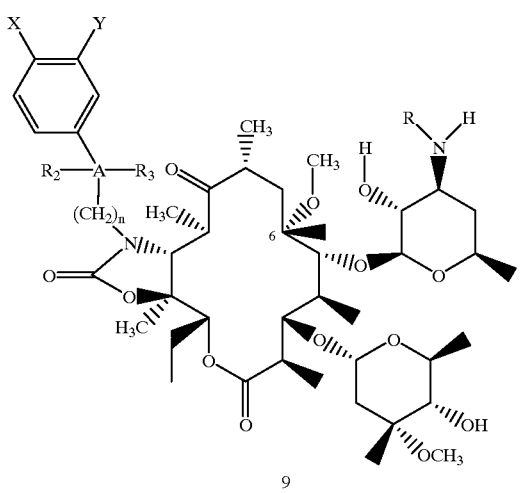

9

Scheme 3 illustrates a specific embodiment of the general scheme described in Scheme 1. As illustrated in Scheme 3, treatment of 2'-acetyl-6-O-methyl erythromycin A 10 with trimethylsilyl chloride affords compound 11. Compound 11 is treated with sodium hexamethyldisilazide and carbonyldiimidazole to yield the 12-O-acylimidazole derivative, which is subsequently reacted with 3,4-dichlorophenethyl amine to form the 11,12-cyclic carbamate derivative. The 11,12 cyclic carbamate so obtained is treated with methanol to give compound 12. Deprotection of the 4"-protected hydroxy group is achieved by methods known in the art to yield compound 13. Treatment of compound 13 with iodine in the presence of sodium acetate followed by quenching the reaction mixture with sodium bisulfite affords compound 14. The second desmethylation is achieved by treating 14 with iodine, tribasic potasium phosphate and a light source to form the bisdesmethyl amine 15. The bisalcylation of the 3'-nitrogen is achieved by reaction with cyclopropanecarboxaldehyde in the presence of sodium cyanoborohydride in methanol and acetic acid to afford the final product, compound 16.

Scheme 3

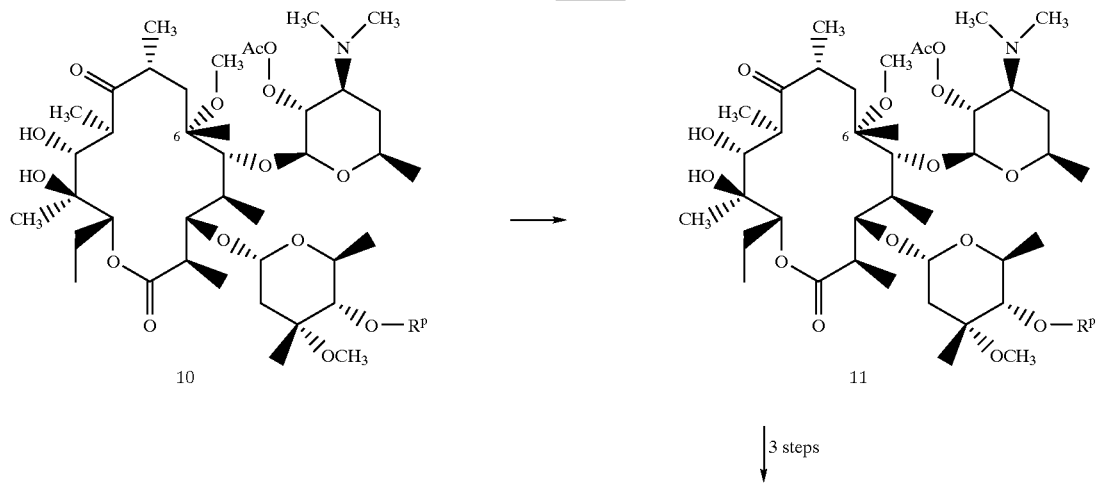

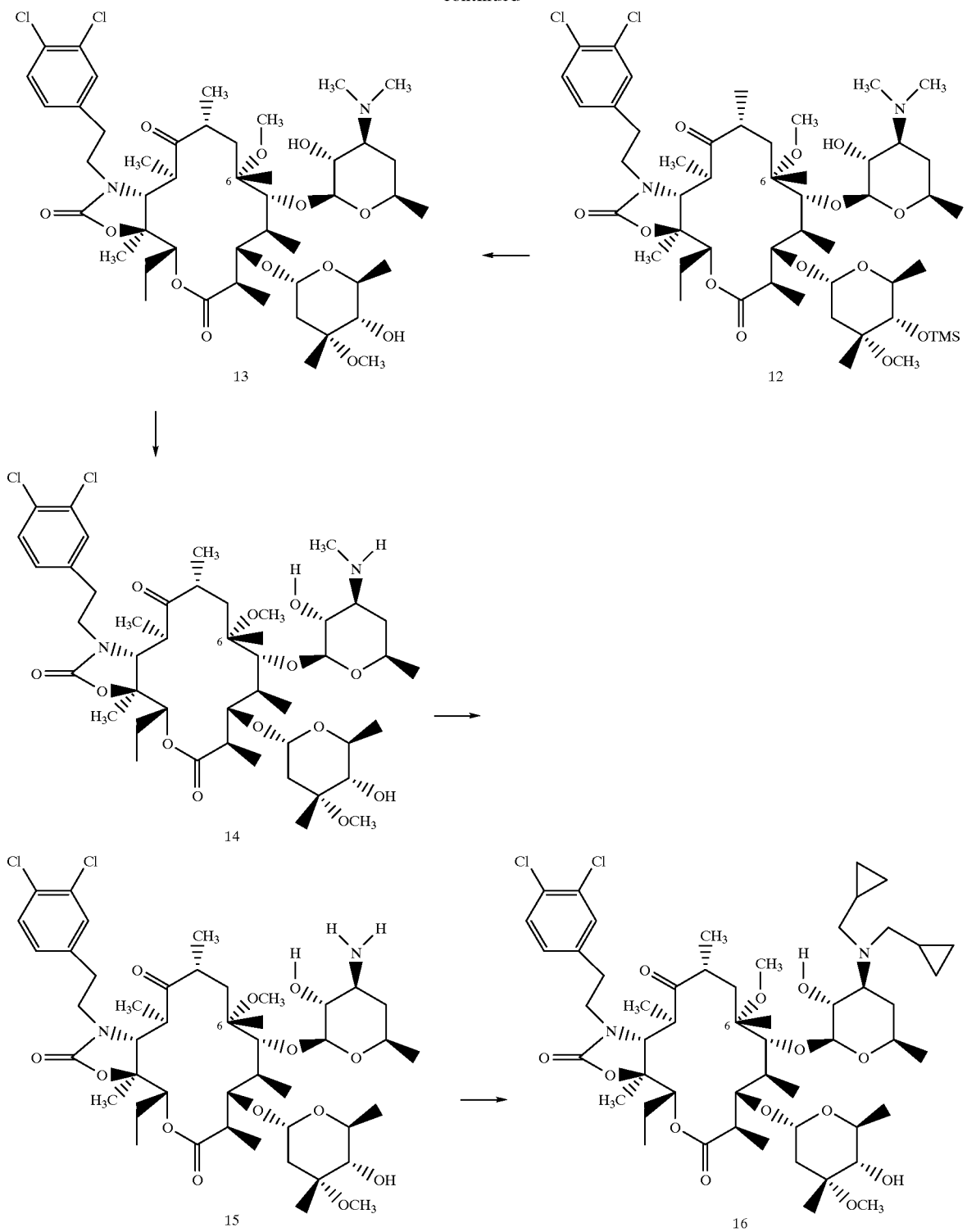

Scheme 4 illustrates a specific embodiment of the general example described in Scheme 2 which involves treatment of 2'-acetyl-6-O-methyl erythromycin A 10 with trimethylsilyl chloride to afford compound 11. Compound 11 is treated with sodium hexamethyldisilazide and carbonyldimidazole to yield the 12-O-acylimidazole derivative, which is subsequently reacted with 4-chlorophenethyl amine to form the 11,12-cyclic carbamate derivative. The 11,12 cyclic carbamate so obtained is treated with methanol to give compound 17. Deprotection of the 4"-protected hydroxy group is achieved by methods known in the art to yield compound 18. Treatment of compound 18 with iodine in the presence of sodium acetate followed by quenching the reaction mixture with sodium bisulfite affords compound 19. The first alkylation is achieved by reaction with acetone in the presence of sodium cyanoborohydride in methanol and a few drops of acetic acid to afford the final product, compound 20. The second dealkylation is achieved by treating 20 with iodine, sodium acetate and a light source to form the desmethyl amine 21. The alkylation of the 3'-nitrogen is achieved by reaction with cyclobutanone in the presence of sodium cyanoborohydride in methanol and acetic acid to afford the final product, compound 22.

Scheme 4

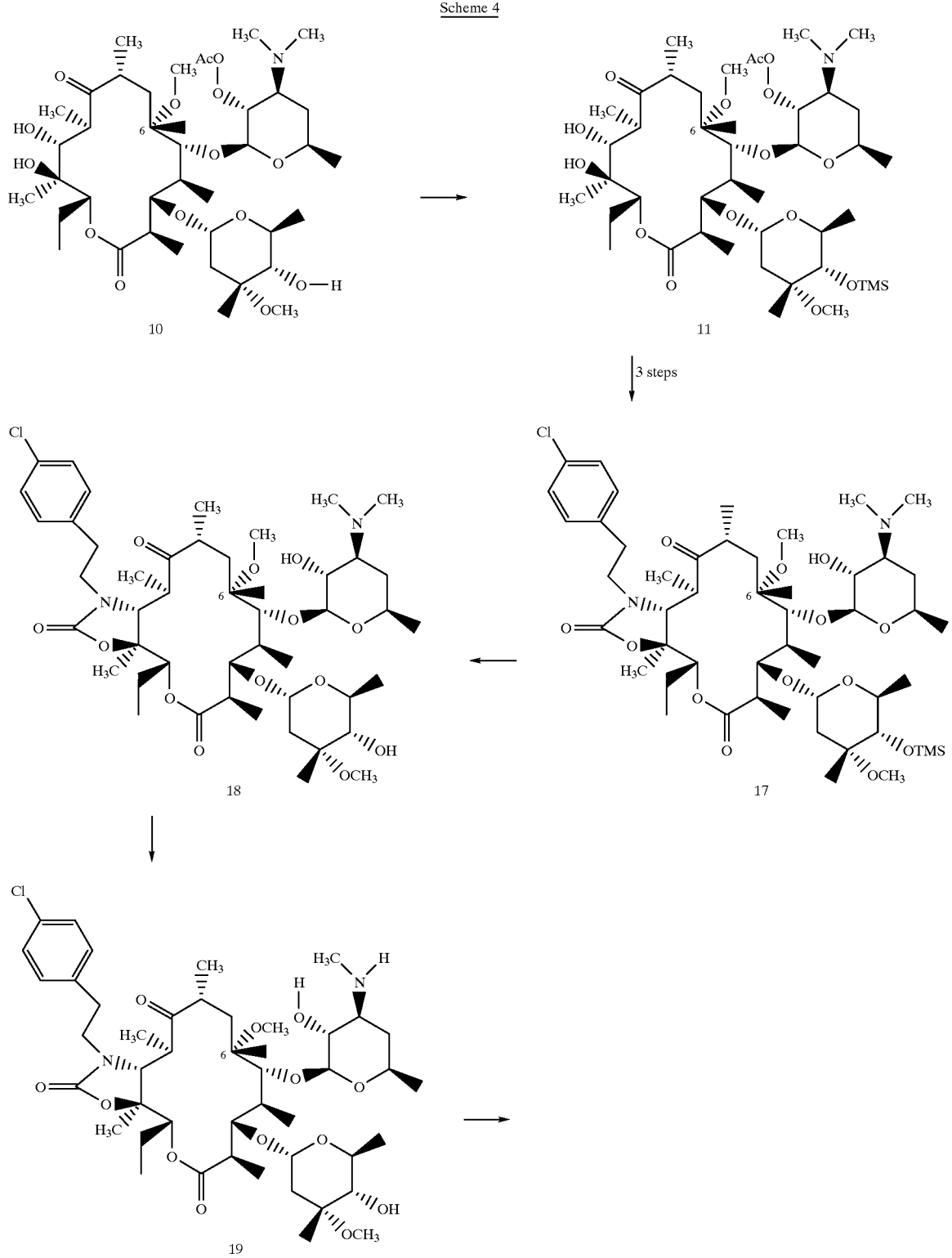

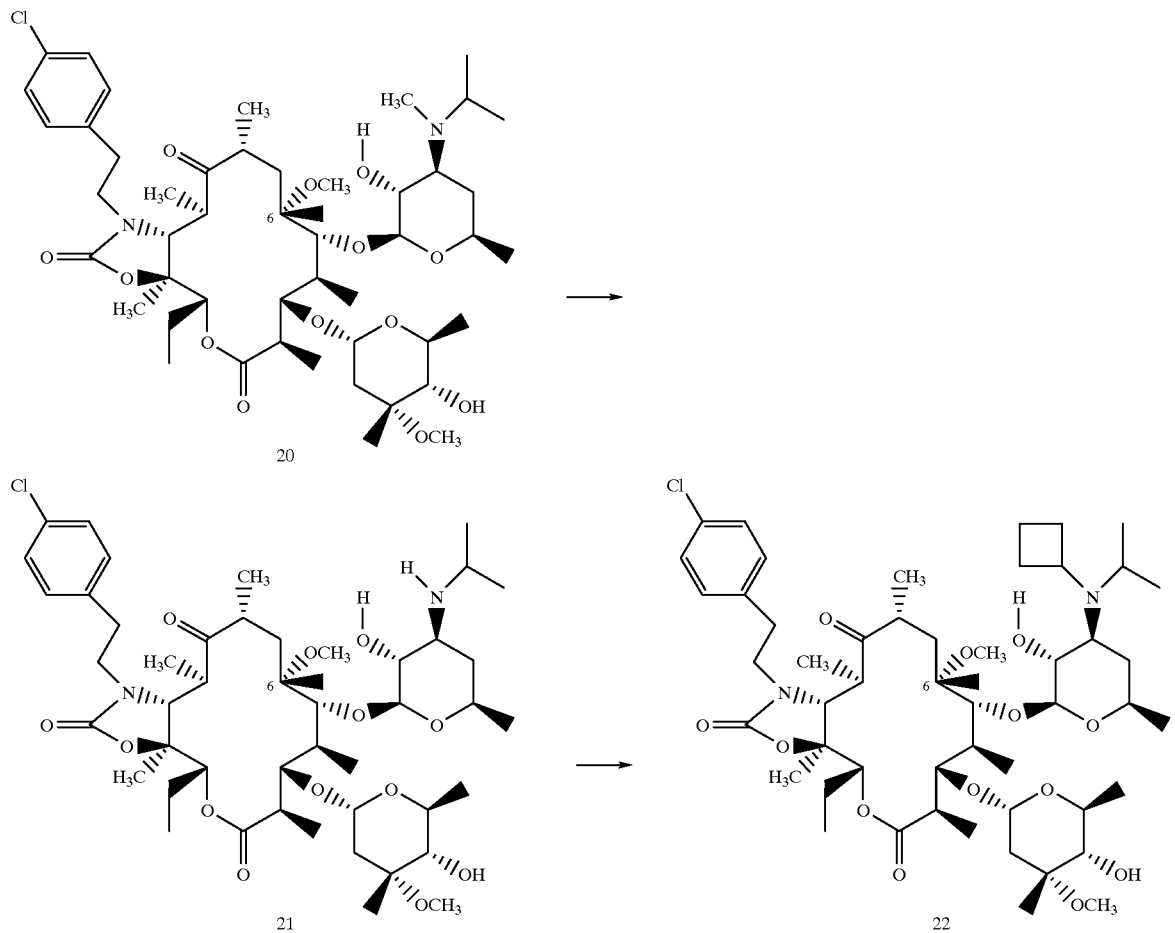
scheme 5 illustrates a third example for a method of preparation for an example described herein. In this example different alkyl groups are added to the amine 23 in a sequential manner to form 25.
Scheme 5
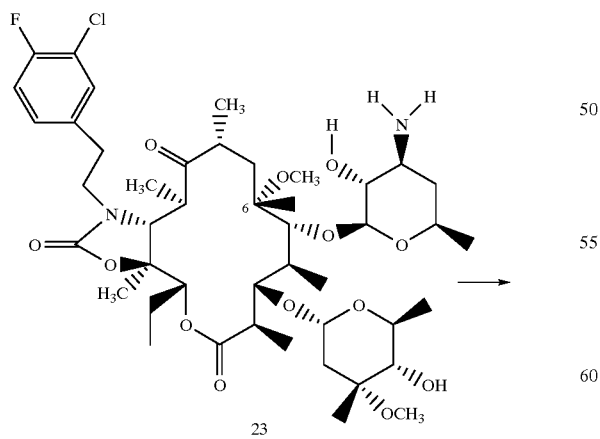
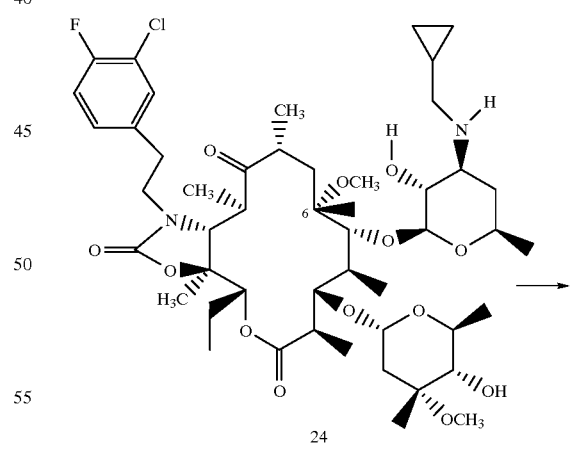

-continued

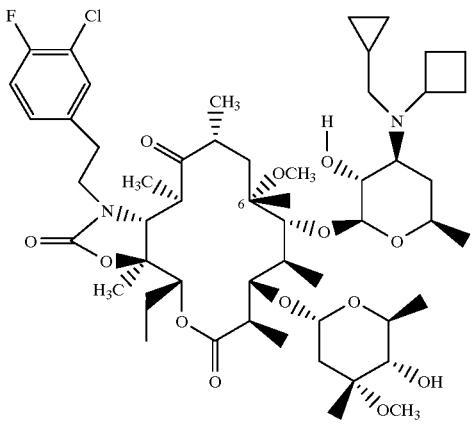

The foregoing may be better understood by reference to the following examples which are presented for illustration and not to limit the scope of the inventive concept.

EXAMPLES

Example 1

3',3'-N-Bisdesmethyl-3,3'-N-biscyclopropylmethyl-11-deoxy-11-[carboxy-(4-chlorophenethylamino) ]-6-O-methyl-eryhromycin A 11,12-(cyclic carbamate)

6-O-methyl erythromycin A (commercially available from Abbott Laboratories as BIAXIN, was protected at the 2'-position with a hydroxy-protecting group by the methods described in the literature.

Step 1: 2'-O-Ac-4"-O-trimethylsilyl-6-O-methyl-erythromycin A (Compound 11, Scheme 3)

2'-O-Ac-6-O-methyl-erythromycin A (45 g, 57 mmol) was dissolved in 450 mL of $CH_2Cl_2$ and cooled to 0° C. in an ice/water bath. Pyridine (13.8 mL, 171 mmol) was added in one portion followed by the dropwise addition of TMSCl (14.5 mL, 114 mmol) over a 15 min period. The reaction was stirred for 1 h under the protection of a drying tube, afterwhich TLC ($CH_2Cl_2$: MeOH, 9:1) indicated complete conversion to a new, less polar material. The reaction was then quenched with 500 mL of 0.5 M $NaH_2PO_4$, the organic layer was separated and washed with $H_2O$ (300 mL), $NaHCO_3$(sat.) (300 mL), $H_2O$ (300 mL), and brine (100 mL), prior to drying ($Na_2SO_4$), filtering and concentrating. The residue was crystallized from $CH_3CN$ to yield 48 g of 11 (98%): mp 235–237° C. ($CH_3CN$); $R_f$=0.5 ($CH_2Cl_2$:MeOH, 9:1); MS (ESI) (M+H)$^+$ at m/z 862; $^{13}C$ NMR (75 MHz, CDCl$_3$) δ 221.0, 175.6, 169.9, 100.0, 96.0, 80.5, 80.3, 78.3, 77.8, 76.4, 74.1, 73.2, 72.0, 69.0, 67.1, 65.2, 62.7, 50.3, 49.4, 45.1, 44.9, 40.5, 38.7, 38.6, 37.1, 35.6, 30.9, 22.1, 21.5, 21.4, 20.9, 19.7, 19.2, 17.8, 15.9, 15.8, 12.1, 10.4, 8.9, 0.8.

Step 2: 4"-O-Trimethylsilyl-11-deoxy-11-[carboxy-(3,4-dichlorophenethylamino)]-6-O-methyl-erythromycin A 11,12-(cyclic carbamate) (Compound 12, Scheme 3)

The compound 11(6.0 g, 6.96 mmol) from the above step was dissolved in 10 mL of anhydrous THF then diluted with 50 mL of DMF. The resulting solution was cooled in an ice/water bath and treated with 1,1'-carbonyldiimidazole (5.64 g, 34.8 mmol) in one portion followed by the portion-wise addition of 1.0 g (25 mmol) NaH (60% suspension). The reaction was allowed to warm to ambient temperature and was stirred under $N_2$ for 1 h afterwhich TLC [EtOAc:MeOH, 95:5, Ce (IV) visualization] indicated complete conversion to a more polar, uv active material. The reaction was carefully quenched with water and then partitioned between EtOAc (300 mL) and water (300 mL). The organic phase was collected and washed with water (2×300 mL), and brine (200 mL) prior to drying ($Na_2SO_4$) and concentration. A sample of the resulting colorless foam was submitted for mass spectral analysis which showed the desired (M+H)$^+$ at m/z 938. The remaining material was dissolved in $CH_3CN$ (25 mL), treated with 5.0 g (26 mmol) of 3,4-dichlorophenethylamine and stirred under $N_2$ at 55° C. After 48 h TLC [EtOAc:MeOH, 95:5, Ce (IV) visualization] indicated complete conversion to a less polar material which precipitated upon cooling to ambient temperature. The resulting precipitate was recrystallized from $CH_3CN$ to yield 5.74 g of protected cyclic carbamate as colorless needles: MS (ESI) (M+H)$^+$ at m/z 1059; $^{13}C$ NMR (75 MHz, CDCl$_3$) δ 216.4, 176.3, 170.1, 157.2, 139.3, 132.2, 131.1, 130.3, 130.1, 128.4, 100.2, 96.3, 82.8, 80.5, 79.9, 79.0, 77.5, 76.2, 73.2, 67.4, 65.4, 62.8, 60.3, 50.5, 49.6, 45.5, 45.3, 44.8, 41.0, 39.0, 38.7, 38.5, 35.7, 32.6, 31.0, 22.2, 21.9, 21.6, 20.2, 19.3, 18.8, 16.1, 14.3, 14.1, 10.2, 9.2, 1.9, 0.8.

The protected cyclic carbamate (5.74 g, 5.42 mmol) was suspended in 250 mL of methanol and the suspension heated to 55° C. under the protection of a drying tube. After 24 h TLC [$CH_2Cl_2$:MeOH, 9:1, Ce (IV) visualization] indicated complete conversion to a new more polar material which crystallized upon cooling to ambient temperature. The resulting solid was crystallized from MeOH/water to yield 5.24 g of the compound 12 (74% from 11): mp 112–114° C.; $R_f$=0.65 ($CH_2Cl_2$:MeOH, 9:1); MS (ESI) (M+H)$^+$ at m/z 1017; HRMS m/z (M+H)$^+$ calcd 999.5116, obsd 999.5110; $^1H$ NMR (300 MHz, CDCl$_3$) δ 7.46 (d, J=2 Hz, Ar H), 7.35 (d, J=8 Hz, Ar H), 7.19 (dd, J=8, 2 Hz, Ar H), 4.91 (d, J=4.4 Hz, 1H), 4.56 (d, J=7 Hz, 1H, C-1' CH), 3.75 (d, J=10 Hz, 1H, C-3 CH), 3.70 (s, 1H, C-11 CH), 3.67 (d, J=8 Hz, 1H, C-5 CH), 3.31 (s, 3H, C-6 OCH$_3$), 3.07 (s, 3H, C-6 OCH$_3$), 2.38 (d, J=15 Hz, 1H, C-2" CH), 2.28 (s, 6H, C-2' N(CH$_3$)$_2$), 1.43 (s, 3H, C-6 CH$_3$), 1.40 (s, 3H, C-12 CH$_3$), 1.07 (d, J=23 Hz, 3H, C-10 CH$_3$), 0.82 (t, J=7 Hz, 3H, C-15 CH$_3$), 0.16 (s, 9H, C-4" OSi(CH$_3$)$_3$); $^{13}C$ NMR (75 MHz, CDCl$_3$) δ 216.1, 176.5, 157.2, 139.3, 132.1, 131.0, 130.2, 130.0, 128.4, 102.4, 96.6, 82.8, 80.6, 79.9, 79.0, 78.0, 76.1, 73.1, 71.1, 68.0, 65.2, 64.7, 60.3, 50.6, 49.6, 45.5, 45.3, 44.8, 40.0 (2C), 39.1, 38.9, 35.6, 32.6, 28.6, 22.1, 21.8, 21.7, 20.1, 19.2, 18.8, 16.0, 14.1, 14.0, 10.2, 9.0, 0.8.

Step 3: 11-Deoxy-11-[carboxy-(3, 4dichlorophenethylamino)]-6-O-methyl-erythromycin A 11,12-(cyclic carbamate) (Compound 13, Scheme 3)

Trimethylsilyl ether 12 (5.24 g, 5.15 mmol) from the above step was dissolved in 50 mL of THF, treated with 5.4 mL of TBAF (1 M/THF, 2.6 mmol), and stirred at ambient temperature. After 2 h TLC [CHCl$_3$:MeOH:NH$_4$OH, 90:8:1, Ce (IV) visualization] indicated complete conversion to a new more polar material. The reaction mixture was partitioned between EtOAc (300 mL) and water (300 mL). The organic phase was washed with NaHCO$_3$ (sat., 200 mL), water (200 mL), and brine (200 mL) prior to drying (Na$_2$SO$_4$) and concentrating. Resulting residue crystallized from CH$_3$CN to yield 4.82 g of the compound 13 (99%): $R_f$=0.45 (CHCl$_3$:MeOH:NH$_4$OH, 90:8:1); mp 240–243° C.; MS (FAB) (M+H)$^+$ at m/z 945; $^1H$ NMR (300 MHz, CDCl$_3$) δ7.45 (d, J=2 Hz, 1H, Ar H), 7.35 (d, J=8 Hz, 1H. Ar H), 7.19 (dd, J=8, 2 Hz, 1H, Ar H), 4.44 (d, J=7 Hz, 1H, C-1' CH), 3.75 (d, J=10 Hz, 1H, C-3 CH), 3.69 (s, 1H, C-11 CH), 3.33 (s, 3H, C-3" OCH$_3$), 3.07 (s, 3H, C-6 OCH$_3$), 2.29 (s, 6H, C-3' N(CH$_3$)$_2$), 2.19 (d, J=10 Hz, 1H, C-4" OH), 1.44 (s, 3H, C-6 CH$_3$), 1.40 (s, 3H, C-12 CH3), 1.31 (d, J=6 Hz, 3H, C-6" CH$_3$), 1.26 (s, 3H, C-3" CH$_3$), 1.15 (d, J=7 Hz, 3H, C-8 CH$_3$), 1.12 (d, J=8 Hz, 3H, C-4CH$_3$),1.02(d,J=7 Hz,3H,C-10 CH$_3$),0.83(t,J=8 Hz,3H,C-15 CH$_3$); $^{13}C$ NMR (75 MHz, CDCl$_3$) δ 216.2, 176.4, 157.2, 139.3, 132.1, 131.0, 130.2, 130.1, 128.4, 102.9, 96.2, 82.8, 80.1, 78.9, 77.9, 77.8, 76.2, 72.6, 70.9, 68.9, 65.8, 65.6, 60.3, 50.6, 49.5, 45.5, 45.3, 44.8, 40.2 (2C), 39.0, 38.9, 34.8, 32.6, 28.5, 21.9, 21.5 (2C), 20.2, 18.9, 18.7, 16.0, 14.2, 14.1, 10.2, 9.0; IR (KBr) υ 3430, 2970, 2940, 1760, 1735, 1710, 1460, 1420, 1380, 1235, 1170, 1070, 1055, 1010, 1000 cm$^{-1}$; Anal. Calcd for $C_{47}H_{74}Cl_2N_2O_{13}$. 0.5 $H_2O$: C, 59.11; H, 7.91; N, 2.93. Found: C, 59.13; H, 8.12; N, 2.89.

Step 4: 3'-N-Desmethyl-11-deoxy-11-[carboxy-(3,4dichlorophenethylamino)]-6-O-methyl-erythromycin A 11,12-(cyclic carbamate) (Compound 14, Scheme 3)

2.5 g of the compound 13 (2.65 mmol) from the above step was dissolved in 50 mL of methanol and treated with 1.80 g of NaOAc.3$H_2O$ (13.25 mmol) and 0.71 g of $I_2$ (2.78 mmol). The solution was irradiated with a 500W halogen work lamp which maintained the reaction at reflux temperature. After 2h TLC indicated complete conversion to a new, more polar material. The excess $I_2$ was quenched by the dropwise addition of 1M $Na_2S_2O_3$. The reaction mixture was concentrated and the resulting residue partitioned between EtOAc (200 mL) and NaHCO$_3$(sat.) (200 mL). The organic phase was washed with brine (100 mL), dried ($Na_2SO_4$), filtered and concentrated. The resulting residue was purified on a silica gel column (elution with CHCl$_3$:MeOH:NH$_4$OH, 90:8:1) to yield 1.75 g of the compound 14 (71%) as an amorphous solid: R$_f$=0.33 (CHCl$_3$:MeOH:NH$_4$OH, 90:8:1); mp 136–142° C. (CH$_3$CN/ $H_2O$); MS (FAB) (M+H)$^+$ at m/z 931; $^1$H NMR (300 MHz, CDCl$_3$) δ 7.45 (d, J=2 Hz, 1H, Ar H), 7.35 (d, J=8 Hz, 1H. Ar H), 7.19 (dd, J=8, 2 Hz, 1H. Ar H), 4.42 (d, J=7 Hz, 1H, C-1' CH), 3.74 (d, J=9 Hz, 1H, C-3 CH), 3.69 (s, 1H, C-11 CH), 3.32 (s, 3H, C-3" OCH$_3$), 3.07 (s, 3H, C-6 OCH$_3$), 2.42 (s, 3H, C-3' NCH$_3$), 1.44 (s, 3H, C-6 CH$_3$), 1.41 (s, 3H, C-12 CH$_3$), 1.31 (d, J=6 Hz, 3H, C-6" CH$_3$), 1.26 (s, 3H, C-3" CH$_3$), 1.16 (d, J=7 Hz, 3H, C-8 CH$_3$), 1.07 (d, J=8 Hz, 3H, C-4 CH$_3$), 1.03 (d, J=7 Hz, 3H, C-10 CH$_3$), 0.82 (t, J=7 Hz, 3H, C-15 CH$_3$); $^{13}$C NMR (75 MHz, CDCl$_3$) δ 216.2, 176.2, 157.1, 139.2, 132.2, 131.0, 130.3, 130.2, 128.4, 102.4, 96.2, 82.7, 80.5, 78.8, 77.8, 77.7, 76.3, 75.0, 72.7, 68.6, 65.7, 60.3, 50.7, 50.6, 49.5, 45.4, 45.3, 44.8, 39.0, 38.9, 38.8, 37.3, 34.8, 33.3, 32.6, 21.9, 21.5, 21.3, 20.1, 18.9, 18.7, 16.0, 14.2, 14.1, 10.2, 9.6; IR (KBr) υ 3420, 2970, 2940, 1760, 1735, 1710, 1460, 1420, 1380, 1235, 1170, 1065, 1050, 1010, 1000 cm$^{-1}$; Anal. Calcd for $C_{46}H_{72}Cl_2N_2O_{13}$.0.75 $H_2O$: C, 56.39; H, 7.44; N, 2.81. Found: C, 56.63; H, 7.36; N, 2.78.

Step 5: 3',3'-N-Bisdesmethyl-11-deoxy-11-[carboxy-(3,4-dichlorophenethylamino)]-6-O-methyl-erythromycin A 11,12-(cyclic carbamate) (Comound 15, Scheme 4)

A solution of 2.07 g (2.19 mmol) of the compound 14 was dissolved in 50 mL of methanol and treated dropwise with a solution of 2.32 g of $K_3PO_4$ (11.0 mmol) in 5 mL $H_2O$ followed by 1.11 g of $I_2$ (4.38 mmol) in a single portion. The solution was irradiated with a 500W halogen work lamp which maintained the reaction at reflux temperature. After 0.75 h the iodine color had dissipated and reverse phase HPLC indicated partial conversion to a new, more polar material. The reaction mixture was concentrated to ⅓ volume and partitioned between ethyl acetate (400 mL) and saturated sodium bicarbonate solution (100 mL). The organic layer was washed with water (300 mL) and brine (300 mL) prior to drying (Na$_2$SO$_4$), filtering and concentrating. The resulting residue was resubjected to the reaction conditions described above. After 1 h the iodine color had dissipated and reverse phase HPLC indicated total conversion to a new, more polar material. The reaction mixture was concentrated to ⅓ volume and partitioned between ethyl acetate (400 mL) and saturated sodium bicarbonate solution (100 mL). The organic layer was washed with water (300 mL) and brine (300 mL) prior to drying (Na$_2$SO$_4$), filtering and concentrating. The resulting residue was crystallized from CH$_3$CN to yield 1.25 g of the compound 15 (62%): mp 223–225° C. (EtOAc); MS (FAB) (M+H)$^+$ at m/z 917; $^1$H NMR (300 MHz, CDCl$_3$) δ 7.46 (d, J=2 Hz, Ar H),7.35(d, J=8 Hz, Ar H),7.19(dd,J=8, 2 Hz, Ar H), 4.39(d, J=7 Hz, C-1' CH), 4.04–3.98 (m, 1H, C-5" CH), 3.32 (s, 3H, C-3" OCH$_3$), 2.68–2.61 (m, 1H, C-8 CH), 1.44 (s, 3H, C-6 CH$_3$), 1.41 (s, 3H, C-12 CH$_3$), 1.06 (d, J=8 Hz, 3H, C-4 CH$_3$), 1.03 (d, J=7 Hz, 3H, C-10 CH$_3$), 0.83 (t, J=7 Hz, 3H, c-15 CH$_3$); $^{13}$C NMR (75 MHz, CDCl$_3$) δ 216.0, 176.1, 157.1, 139.1, 132.1, 130.9, 130.2, 130.1, 128.3, 102.3, 96.1, 82.7, 80.5, 78.8, 77.8, 77.7, 77.3, 76.3, 72.6, 68.5, 65.7, 60.3, 52.4, 50.6, 49.3, 45.3, 45.2, 44.7, 41.3, 38.9, 38.7, 34.7, 32.5, 21.8, 21.4, 21.0, 20.0, 18.8, 18.6, 15.9, 14.2, 14.1, 10.1, 9.6; IR (KBr) υ 3440, 2970, 2930, 1760, 1735, 1165, 1065, 1010 cm$^{-1}$.

Step 6: 3',3'-N-Bisdesmethyl-3',3'-N-biscyclopropylmethyl-11-deoxy-11-[carboxy-(4-chlorophenethylamino)]-6-O-methyl-erythromycin A 11,12-(cyclic carbamate) (Compound 16, Scheme 3).

290 mg (0.32 mmol) of the compound 15 from the above step was dissolved in 15 mL of methanol and treated with cyclopropanecarboxaldehyde (460 mg, 6.6 mmol), sodium cyanoborohydride (80 mg, 1.3 mmol) and acetic acid (7 drops to pH 5–6) and the mixture stirred at ambient temperature. After 24 h TLC [CHCl$_3$:MeOH, 98:2, Ce (IV) visualization] indicated complete conversion to a new, less polar material. The reaction was concentrated and the resulting residue partitioned between ethyl acetate (159 mL) and water (150 mL). The organic layer was washed with water (150 mL), and brine (150 mL) prior to drying (Na$_2$SO$_4$), filtering and concentrating. The resulting residue was purified on a silica gel column (elution with CHCl$_3$:MeOH:NH$_4$OH, 90:8:1) and crystallized from acetonitrile to yield 180 mg of 16 (56%) as fine needles: MS (FAB)(M+H)$^+$ at m/z 1025; $^1$H NMR (300 MHz, CDCl$_3$) δ 7.46 (d, J=2 Hz, 1H), 7.35 (d, J=8, 1H), 7.20 (dd, J=8, 1.8, 1H), 4.93 (d, J=5, 1H), 4.90 (dd, J=9, 2.2, 1H), 4.49 (d, J=7, 1H), 4.05–4.02 (m, 1H), 3.90–3.81 (series of m, 3H), 3.75 (d, J=10, 1H), 3.70 (s, 1H), 3.67 (d, J=7, 1H), 3.51–3.48 (m, 1H), 3.34 (s, 3H), 3.17–3.12 (series of m, 2H), 3.07 (s, 3H), 3.05–2.87 (series of multiplets, 5H), 2.64–2.59 (series of m, 3H), 2.38 (d, J=15, 1H), 2.22 (d, J=7, 1H), 2.19 (d, J=7, 1H) 2.14 (d, J=10, 1H), 1.94–1.87 (series of multiplets, 2H), 1.78–1.76 (series of m, 2H), 1.66–1.52 (series of m, 4H), 1.43 (s, 3H), 1.40 (s, 3H), 1.31 (d, J=6, 3H), 1.26–1.20 (series of multiplets, 9H), 1.17–1.15 (series of m, 6H), 1.03 (d, J=7.0, 3H), 0.86–0.81 (series of m, 5H), 0.57 (t, J=10.0, 2H), 0.47 (t, J=10.0, 2H), 0.13–0.11 (m, 4H); $^{13}$C NMR (CDCl$_3$) δ 216.3, 176.3, 157.2, 139.3, 132.2, 131.0, 130.3, 130.1, 128.4, 103.1, 96.0, 82.8, 80.3, 78.9, 77.8, 76.2, 72.6, 70.4, 69.1, 65.8, 61.7, 60.4, 54.5, 50.6, 49.5, 45.6, 45.3, 44.8, 39.1, 39.0, 39.0, 34.8, 32.6, 30.3, 21.9, 21.5, 21.5, 20.2, 18.9, 18.6, 16.0, 14.2, 14.1, 10.4, 10.2, 9.0, 5.5, 2.7; Anal. Calcd for $C_{53}H_{82}Cl_2 N_2O_{13}$: C, 62.04; H, 8.05; N, 2.73. Found: C, 61.66; H, 8.10 N, 2.59.

EXAMPLE 2

3',3'-N-Bisdesmethyl-3',3'-N-biscyclobutyl-11-deoxy-11-[carboxy-(4-chlorophenethylamino)]-6-O-methyl-erythromycin A 11,12-(cyclic carbamate)

The title compound was prepared according to the procedure described in Example 1 except substituting cyclobutanone for cyclopropanecarboxaldehyde. Product purified on a silica gel column to yield an amorphous solid: R$_f$=0.58 (CHCl$_3$:MeOH:NH$_4$OH 94:5:1); IR (KBr),) υ 3440, 2960, 2925, 1755, 1730, 1460, 1380, 1165, 1105, 1065, 1050 cm$^{-1}$; $^1$H NMR (400 MHz, CDCl$_3$) δ 7.45 (d, J=2 Hz, 1H), 7.34 (d, J=8, Hz 1H), 7.19 (dd, J=8, 2 Hz, 1H), 4.92 (d, J=5 Hz, 1H), 4.89 (dd, J=11, 2 Hz, 1H), 4.40 (d, J=7 Hz, 1H), 4.02–3.99 (m, 1H), 3.88–3.78 (m, 2H), 3.72 (d, J=10 Hz, 1H), 3.69 (s, 1H), 3.65 (d, J=7, 1H), 3.47–3.44 (m, 1H), 3.33

(s, 3H), 3.31–3.26 (series of m, 2H), 3.12 (q, J=7 Hz, 2H) 3.07 (s, 3H), 3.05–2.84 (series of multiplets, 6H), 2.65–2.61 (m, 1H), 2.50 (broad singlet, 1H), 2.38 (d, J=7 Hz, 1H), 2.14–1.43 (series of multiplets, 21H), 1.41 (s, 3H), 1.40 (s, 3H), 1.30 (d, J=6 Hz, 3H), 1.24–1.20 (series of multiplets, 11H), 1.15 (d, J=7 Hz, 3H), 1.11 (d, J=7 Hz, 3H), 0.82 (t, J=7 Hz, 3H); $^{13}$C NMR (75 MHz, CDCl$_3$) δ 216.4, 176.3, 157.2, 139.2, 132.1, 131.0, 130.2, 130.1, 128.4, 103.3, 95.9, 82.8, 80.3, 78.8, 77.8, 77.7, 76.2, 72.6, 70.7, 69.2, 65.7, 60.3, 58.8, 54.3, 50.6, 49.5, 45.5, 45.2, 44.7, 39.0, 38.9, 38.8, 34.8, 32.6, 31.2, 30.0, 29.7, 21.9, 21.5, 20.1, 18.9, 18.6, 16.0, 15.6, 14.2, 14.1, 10.2, 9.0; MS (FAB) (M+H)$^+$ at m/z 1025; Anal. Calcd for C$_{53}$H$_{82}$Cl$_2$ N$_2$O$_{13}$ C, 62.04; H, 8.05; N, 2.73. Found: C, 61.94; H, 8.24 N, 2.61.

EXAMPLE 3

3',3'-N-Bisdesmethyl-3',3'-N-biscyclolpropylmethyl-11-deoxy-11-[carboxy-(4-chlorophenetlylamino)]-6-methyl-eryromycin A 11,12-(cyclic carbamate)

The title compound was prepared as described in Example 1 but substituting 4-chlorophenethylamine for 3,4-dichlorophenethylamine. Product crystallized from CH$_3$CN/H$_2$O: R$_f$=0.38 (8% MeOH/DCM, 0.1% NH$_4$OH); IR (KBr) υ 3440, 2970, 2940, 1765, 1735, 1715, 1490, 1460, 1420, 1380, 1330, 1280, 1235, 1170, 1130, 1110, 1095, 1070, 1055, 1015, 1000 cm$^{-1}$; $^1$H NMR (300 MHz, CDCl$_3$) δ 7.30–7.22 (series of m, 4H), 4.96–4.92 (series of m, 2H), 4.40 (d, J=67.1 Hz, 1H), 4.04–3.97 (m, 1H), 3.87–3.80 (m, 2H), 3.75–3.70 (series of m, 3H), 3.64 (d, J=7.5 Hz, 1H), 3.50–3.40 (m, 1H), 3.34 (s, 3H), 3.28–3.20 (m, 2H), 3.20–3.09 (m, 2H), 3.07 (s, 3H), 3.06–2.80 (series of m, 5H), 2.68–2.57 (m, 1H), 2.54–2.43 (m, 1H), 2.38 (d, J=15.3 Hz, 1H), 2.10 (d, J=10.2 Hz, 1H), 2.08–1.98 (series of m, 3H), 1.97–1.82 (series of m, 6H), 1.80–1.74 (m, 2H), 1.67–1.50 (series of m, 7H), 1.42 (s, 3H), 1.40 (s, 3H), 1.29 (d, J=6.1 Hz, 3H), 1.25 (s, 3H), 1.22 (d, J=6.4 Hz, 3H), 1.20 (d, J=5.8 Hz, 3H), 1.15 (d, J=7.1 Hz, 3H), 1.13 (d, J=7.8 Hz, 3H), 1.02 (d, J=6.8 Hz, 3H), 0.83 (t, J=7.3 Hz, 3H); $^{13}$C NMR (75 MHz, CDCl$_3$) δ 216.2, 176.3, 157.2, 137.5, 131.9, 130.3, 128.5, 103.4, 96.0, 82.8, 80.4, 78.9, 77.9, 77.8, 76.3, 72.7, 70.9, 69.3, 65.8, 60.4, 58.9, 50.7, 49.5, 45.6, 45.3, 45.0, 39.1, 39.0, 34.9, 32.9, 32.7, 31.2, 30.1, 22.0, 21.5, 20.2, 18.9, 18.6, 16.0, 15.7, 14.2, 14.1, 10.3, 9.0; MS (FAB) (M+H)$^+$ at m/z 991; Anal. Calcd for C$_{53}$H$_{83}$ Cl N$_2$O$_{13}$: C, 64.19; H, 8.44; N, 2.82. Found: C, 64.10; H, 8.54; N, 2.79.

EXAMPLE 4

3',3'-N-Bisdesmethyl-3',3'-N-biscyclobutyl-11-deoxy-11-[carboxy-(4-chlorophenethylamino)]-6-O-methyl-erythromycin A 11,12-(cyclic carbamate)

The title compound was prepared as described in Example 2 but substituting 4-chlorophenethylamine for 3,4-dichlorophenethylamine. Product crystallized from CH$_3$CN/H$_2$O: R$_f$=0.38 (8% MeOH/DCM, 0.1% NH$_4$OH); IR (KBr) υ 3440, 2970, 2940, 1765, 1735, 1715, 1490, 1460, 1420, 1380, 1330, 1280, 1235, 1170, 1130, 1110, 1095, 1070, 1055, 1015, 1000 cm$^{-1}$; $^1$H NMR (300 MHz, CDCl$_3$) δ 7.30–7.22 (series of m, 4H), 4.96–4.92 (series of m, 2H), 4.40 (d, J=67.1 Hz, 1H), 4.04–3.97 (m, 1H), 3.87–3.80 (m, 2H), 3.75–3.70 (series of m, 3H), 3.64 (d, J=7.5 Hz, 1H), 3.50–3.40 (m, 1H), 3.34 (s, 3H), 3.28–3.20 (m, 2H), 3.20–3.09 (m, 2H), 3.07 (s, 3H), 3.06–2.80 (series of m, 5H), 2.68–2.57 (m, 1H), 2.54–2.43 (m, 1H), 2.38 (d, J=15.3 Hz, 1H), 2.10 (d, J=10.2 Hz, 1H), 2.08–1.98 (series of m, 3H), 1.97–1.82 (series of m, 6H), 1.80–1.74 (m, 2H), 1.67–1.50 (series of m, 7H), 1.42 (s, 3H), 1.40 (s, 3H), 1.29 (d, J=6.1 Hz, 3H), 1.25 (s, 3H), 1.22 (d, J=6.4 Hz, 3H), 1.20 (d, J=5.8 Hz, 3H), 1.15 (d, J=7.1 Hz, 3H), 1.13 (d, J=7.8 Hz, 3H), 1.02 (d, J=6.8 Hz, 3H), 0.83 (t, J=7.3 Hz, 3H); $^{13}$C NMR (75 MHz, CDCl$_3$) δ 216.2, 176.3, 157.2, 137.5, 131.9, 130.3, 128.5, 103.4, 96.0, 82.8, 80.4, 78.9, 77.9, 77.8, 76.3, 72.7, 70.9, 69.3, 65.8, 60.4, 58.9, 50.7, 49.5, 45.6, 45.3, 45.0, 39.1, 39.0, 34.9, 32.9, 32.7, 31.2, 30.1, 22.0, 21.5, 20.2, 18.9, 18.6, 16.0, 15.7, 14.2, 14.1, 10.3, 9.0; MS (FAB) (M+H)+at m/z 991; Anal. Calcd for C$_{53}$H$_{83}$ Cl N$_2$O$_{13}$: C, 64.19; H, 8.44; N, 2.82. Found: C, 64.10; H, 8.54; N, 2.79.

EXAMPLE 5

3',3'-N-Bisdesmethyl-3'-N-cyclobutyl-3'-N-isopropyl-11-deoxy-11-[carboxy-(4-chlorophenethylamino)]-6-O-methyl-erythromycin A 11,12-(cyclic carbamate)

Step 1: 4"-O-Trimethylsilyl-11-deoxy-11-[carboxy-(4-chlorophenethylamino)]-6-O-methyl-erythromycin A 11,12-(cyclic carbamate) (Compound 17, Scheme 4)

The compound 11 (10.2 g, 11.8 mmol) obtained in Example 1 was dissolved in 10 mL of anhydrous THF then diluted with 60 mL of DMF. The resulting solution was cooled in an ice/water bath and treated with 1,1'-carbonyldiimidazole (9.8 g, 60.4 mmol) in one portion followed by the portionwise addition of 1.8 g (45 mmol) NaH (60% suspension). The reaction was allowed to warm to ambient temperature and was stirred under N$_2$ for 1 h afterwhich TLC [EtOAc:MeOH, 95:5, Ce (IV) visualization] indicated complete conversion to a more polar, uv active material. The reaction was carefully quenched with water and then partitioned between EtOAc (300 mL) and water (300 mL). The organic phase was collected and washed with water (3×300 mL), and brine (200 mL) prior to drying (Na$_2$SO$_4$) and concentration. A sample of the resulting colorless foam was submitted for mass spectral analysis which showed the desired (M+H)$^+$ at m/z 938. The remaining material was dissolved in 10 mL of THF, diluted with CH$_3$CN (40 mL), treated with 18.0 g (115.7 mmol) of 4-chlorophenethylamine and stirred under N$_2$ at 50° C. After 18 h TLC [CH$_2$Cl$_2$:MeOH, 9:1, Ce (IV) visualization] indicated complete conversion to a less polar material. The reaction mixture was then partitioned between EtOAc (300 mL) and 0.5 N NaH$_2$PO$_4$ (400 mL). The organic phase was collected and washed with additional 0.5 N NaH$_2$PO$_4$ (400 mL), water (5×300 mL), and brine (200 mL) prior to drying (Na$_2$SO$_4$) and concentration. The resulting residue was recrystallized from CH$_3$CN to yield 7.4 g (61% from 11) of protected cyclic carbamate as colorless needles. The protected cyclic carbamate was suspended in 75 mL of methanol and the suspension heated to 50° C. under the protection of a drying tube. After 18 h TLC [CH$_2$Cl$_2$:MeOH, 9:1, Ce (IV) visualization] indicated complete conversion to a new more polar material which crystallized upon cooling to ambient temperature. The resulting solid was crystallized from CH$_3$CN to yield 6.75 g of the compound 17 (58% from 11): R$_f$=0.45 (CH$_2$Cl$_2$:MeOH, 9:1); MS (DCI) (M+H)$^+$ at m/z 983.

Step 2: 11-Deoxy-11-[carboxy-(4-chlorophenethylano)]-6-O-methyl-erythromycin A 11,12-(cyclic carbamate) (Compound 18, Scheme 4).

The trimethylsilyl ether 17 (6.75 g, 6.87 mmol) obtained in Step 1 was dissolved in 50 mL of THF, treated with 7.5 mL of TBAF (1 M/THF, 7.5 mmol), and stirred at ambient temperature. After 1 h TLC [CH$_2$Cl$_2$:MeOH, 9:1, Ce (IV) visualization] indicated complete conversion to a new more polar material. The reaction mixture was partitioned between EtOAc (300 mL) and 10% NaHCO$_3$ (100 mL). The organic phase was washed with water (2×300 mL), and brine (200 mL) prior to drying (Na$_2$SO$_4$) and concentrating. Resulting residue crystallized from CH$_3$CN to yield 6.04 of the compound 18 (97%): $R_f$=0.15 ($CH_2Cl_2$:MeOH, 9:1); MS (DCI) $(M+H)^+$ at m/z 911.

Step 3: 3'-N-Desmethyl-11-deoxy-11-[carboxy-(4-chlorophenethylamino)]-6-O-methyl-erythromycin A 11,12-(cyclic carbamate) (Cmpound 19, Scheme 4)

6.04 g of the compound 18 (6.63 mmol) from the above step was dissolved in 60 mL of methanol and treated with 4.52 g of $NaOAc.3H_2O$ (33.2 mmol) and 1.69 g of $I_2$ (6.66 mmol). The solution was irradiated with a 500W halogen work lamp which maintained the reaction at reflux temperature. After 3h TLC ($CHCl_3$:MeOH:$NH_4OH$, 90:8:1) indicated complete conversion to a new, more polar material. The excess $I_2$ was quenched by the dropwise addition of 1M $NaHSO_3$. The reaction mixture was concentrated and the resulting residue partitioned between $CH_2Cl_2$ (300 mL) and $H_2O$ (300 mL). The organic phase was washed with $NaHCO_3$ (sat.) (300 mL), brine, dried ($Na_2SO_4$), filtered and concentrated to yield 5.41 g (91%) of the compound 19: $R_f$=0.15 ($CHCl_3$:MeOH:$NH_4OH$, 90:8: 1); MS (DCI) $(M+H)^+$ at m/z 897.

Step 4: 3'-N-Desmethyl-3'-N-isopropyl-11-deoxy-11-[carboxy-(4-chlorophenethyl-amino)]-6-O-methyl-erythromycin A 11,12-(cyclic carbamate) (Compound 20, Scheme 4)

5.40 g (6.03 mmol) of the compound 19 was dissolved in 50 nL of methanol and treated with acetone (7.0 g, 120 mmol), sodium cyanoborohydride (454 mg, 7.23 mmol) and acetic acid (dropwise to pH 5–6) and the mixture stirred at ambient temperature. After 24 h TLC [$CHCl_3$:MeOH, 98:2, Ce (IV) visualization] indicated complete conversion to a new, less polar material. The reaction was concentrated and the resulting residue partitioned between $CH_2Cl_2$ (300 mL) and water (250 mL). The organic layer was washed with $NaHCO_3$ (sat.) (200 mL), and brine (150 mL) prior to drying ($Na_2SO_4$), filtering and concentrating. The resulting residue was purified on a silica gel column (elution with $CHCl_3$:MeOH:$NH_4OH$, 90:8:1) and crystallized from acetonitrile to yield 4.23 g (75%) of the compound 20: $R_f$=0.80 ($CHCl_3$:MeOH:$NH_4OH$, 90:8:1); MS (DCI) $(M+H)^+$ at m/z 939.

Step 5: 3',3'-N-Bisdesmethyl-3'-N-isopropyl-11-deoxy-11-[carboxy-(4-chlorophenethylamino)]-6-O-methyl-erythromycin A 11,12-(cyclic carbamate) (Compound 21, Scheme 4)

1.6 g of the compound 20 (1.7 mmol) was dissolved in 50 mL of methanol and treated with 1.16 g of $NaOAc.3H_2O$ (8.5 mmol) and 0.48 g of $I_2$ (1.88 mmol). The solution was irradiated with a 500W halogen work lamp which maintained the reaction at reflux temperature. After 3 h TLC ($CHCl_3$:MeOH:$NH_4OH$, 90:8:1) indicated complete conversion to a new, more polar material. The excess $I_2$ was quenched by the dropwise addition of 1M $NaHSO_3$. The reaction mixture was concentrated and the resulting residue partitioned between $CH_2Cl_2$ (300 mL) and $NaHCO_3$ (sat.) (300 mL). The organic phase was washed with $H_2O$ (300 mL), brine, dried ($Na_2SO_4$), filtered and concentrated to yield 1.13 g (71%) of the compound 21: $R_f$=0.50 ($CHCl_3$:MeOH:$NH_4OH$, 90:8:1); MS (DCI) $(M+H)^+$ at m/z 925.

Step 6: 3',3'-N-Bisdesmethyl-3'-N-cyclobutyl-3'-N-isopropyl-11-deoxy-11-[carboxy-(4-chlorophenethylamino)]-6-O-methyl-erythromycin A 11,12-(cyclic carbamate) (Compound 22, Scheme 4)

110 mg (0.119 mmol) of the compound 21 from the above step was dissolved in 50 mL of methanol and treated with cyclobutanone (1.0 g, 14.3 mmol), sodium cyanoborohydride (15 mg, 0.24 mmol) and acetic acid (dropwise to pH 5–6) and the mixture stirred at ambient temperature. After 72 h TLC [$CHCl_3$:MeOH, 98:2, Ce (IV) visualization] indicated conversion to a new, less polar material. The reaction was concentrated and the resulting residue partitioned between EtOAc (100 mL) and water (100 mL). The organic layer was washed with brine (50 mL) prior to drying ($Na_2SO_4$), filtering and concentrating. The resulting residue was purified on a silica gel column eluting with $CHCl_3$:MeOH:$NH_4OH$ (90:8:1) to yield 65 mg (56%) of 22: $R_f$=0.95 $CHCl_3$:MeOH:$NH_4OH$, (90:8:1); MS (ESI)$(M+H)^+$ at m/z 979; HRMS m/z $(M+H)^+$ calcd 979.5662, obsd 979.5660; Anal. Calcd for $C_{52}H_{83}$ Cl $N_2O_{13}$: C, 63.75; H, 8.53; N, 2.85. Found: C, 63.48; H, 8.71; N, 2.79.

EXAMPLE 6

3',3'-N-Bisdesmethyl-3'-N-isopropyl-3'-N-propyl-11-deoxy-11-[carboxy-(4-chlorophenethylamino)]-6-O-methyl-erythromycin A 11,12-(cyclic carbamate)

The title compound was prepared as described in Example 5 but substituting propionaldehyde for cyclobutanone: $R_f$=0.35 ($CHCl_3$:MeOH:$NH_4OH$, 90:8:1); MS (ESI)$(M+H)^+$ at m/z 967.

EXAMPLE 7

3',3'-N-Bisdesmethyl-3'-N-cyclopropylmethyl-3'-N-isopropyl-11-deoxy-11-carboxy-(4-chlorophenethylamino)]-6-O-methyl-erythromycin A 11,12-(cyclic carbamate)

The title compound was prepared as described in Example 5 but substituting cyclopropanecarboxaldehyde for cyclobutanone: mp 211–213° C. ($CH_3CN$); $R_f$=0.85 ($CH_2Cl_2$:MeOH, 9:1); MS (FAB)$(M+H)^+$ at m/z 979; HRMS m/z $(M+H)^+$ calcd 979.5662, obsd 979.5659; IR (KBr) υ 3440, 2965, 2930, 1760, 1735, 1715, 1460, 1380, 1235, 1170, 1090, 1065, 1055, 1015 $cm^{-1}$; $^{13}C$ NMR ($CDCl_3$) δ 216.4, 176.4, 157.2, 137.4, 131.8, 130.3, 128.4, 103.0, 95.9, 82.7, 80.2, 78.8, 77.9, 77.7, 76.2, 72.6, 70.5, 69.1, 65.7, 60.3, 59.6, 50.7, 49.5, 49.2, 47.5, 45.6, 45.2, 45.0, 39.0, 38.9 (2C), 34.8, 34.3, 32.8, 22.9, 21.9, 21.5, 21.4, 20.2, 18.9, 18.6, 16.0, 14.2, 14.1, 11.1, 10.3, 9.0, 5.7, 2.5; Anal. Calcd for $C_{52}H_{85}C_{52}H_{85}ClN_2O_{13}$: C, C, 63.75; H, 8.53; N, 2.85. Found: C, 63.45; H, 8.36; N, 2.72.

EXAMPLE 8

3',3'-N-Bisdesmethyl-3'-N-ethyl-3'-N-isopropyl-11-deoxy-11-[carboxy-(4-chlorophenethylamino)]-6-O-methyl-erythromycin A 11,12-(cyclic carbamate)

The title compound was prepared as described in Example 5 but substituting acetaldehyde for cyclobutanone: mp 225–229° C. ($CH_3CN/H_2O$); $R_f$=0.70 ($CH_2Cl_2$:MeOH, 9:1); MS (ESI)$(M+H)^+$ at m/z 953; IR (KBr) υ 3440, 2960, 2930, 1760, 1735, 1715, 1460, 1380, 1235, 1170, 1100, 1090, 1065, 1055, 1015 $cm^{-1}$; $^{13}C$ NMR ($CDCl_3$) δ 216.2, 176.3, 157.2, 137.5, 131.9, 130.3, 128.5, 103.0, 96.0, 82.7, 80.2, 78.9, 77.9, 77.8, 76.3, 72.7, 70.6, 69.1, 65.8, 60.4, 59.9, 50.7, 49.5, 47.9, 45.6, 45.3, 45.0, 39.1, 39.0 (2C), 38.2, 34.9, 34.5, 32.9, 22.9, 21.9, 21.5, 21.4, 20.1, 19.0, 18.9, 18.7, 15.9, 15.7, 14.2, 14.1, 10.3, 8.9.

EXAMPLE 9

3',3'-N-Bisdesmethyl-3'-N-cyclobutylmethyl-3'-N-cyclopropylmethyl-11-deoxy-11-[carboxy-(4-chlorophenethylamino)]-6-methyl-erythromycin A 11,12-(cyclic carbamate)

The title compound was prepared as described in Example 5 but substituting cyclobutylcarboxaldehyde for acetone and cyclopropanecarboxaldehyde for cyclobutanone: $R_f$=0.65 ($CH_2Cl_2$:MeOH, 9:1); MS (APCI)$(M+H)^+$ at m/z 1005; IR (KBr) υ 3440, 2970, 2930, 1760, 1735, 1710, 1460, 1580, 1380, 1235, 1170, 1100, 1090, 1065, 1055, 1015 cm$^{-1}$; $^{13}$C NMR (CDCl$_3$) δ 216.2, 176.3, 157.1, 137.4, 131.8, 130.3, 128.4, 103.0, 95.9, 82.7, 80.2, 78.8, 77.9, 77.7, 76.2, 72.6, 70.4, 69.0, 65.7, 62.0, 60.3, 55.4, 54.9, 50.6, 49.4, 45.5, 45.2, 44.9, 39.0 (2C), 38.9, 34.8, 34.3, 32.8, 30.1, 27.0, 26.6, 21.9, 21.5, 21.4, 20.1, 18.8, 18.6, 18.5, 16.0, 14.2, 14.1, 10.3, 10.2, 8.9, 5.4, 2.6.

EXAMPLE 10

3',3'-N-Bisdesmethyl-3',3'-N-biscyclopropylmethyl-11-deoxy-11-[carboxy-(4-methoxyphenethylamino)]-6-O-methyl-erythromycin A 11,12-(cyclic carbamate)

The title compound was prepared as described in Example 1 but substituting 4-methoxyphenethylanine for 3,4-dichlorophenethylamine. Product crystallized from CH$_3$CN/H$_2$O: R$_f$=0.53 (8% MeOH/DCM, 0.1% NH$_4$OH); IR (KBr) 3440, 2965, 2935, 1755, 1735, 1705, 1610, 1515, 1455, 1380, 1325, 1250, 1235, 1165, 1110, 1070, 1050, 1010, 1000 cm$^{-1}$; $^1$H NMR (300 MHz, CDCl$_3$) δ 7.24 (d, J=8.8 Hz, 2H), 6.83 (d, J=8.8 Hz, 2H), 4.98 (dd, J=10.9, 2.4 Hz, 1H), 4.92 (d, J=4.4 Hz, 1H), 4.49 (d, J=67.2 Hz, 1H), 4.08–3.97 (m, 1H), 3.90–3.78 (m, 2H), 3.78 (s, 3H), 3.73 (s, 2H), 3.66 (d, J=7.2 Hz, 1H), 3.55–3.44 (m, 1H), 3.33 (s, 3H), 3.18–3.10 (m, 2H), 3.09 (s, 3H), 3.07–2.78 (series of m, 5H), 2.70–2.56 (series of m, 3H), 2.37 (d, J=15.3 Hz, 1H), 2.21 (d, J=7.1 Hz, 1H), 2.17 (d, J=6.8 Hz, 1H), 2.13 (d, J=10.2 Hz, 1H), 2.02–1.86 (m, 2H), 1.77 (d, J=6.5 Hz, 1H), 1.68–1.46 (series of m, 4H), 1.42 (s, 3H), 1.40 (s, 3H), 1.30 (d, J=6.1 Hz, 3H), 1.25 (s, 3H), 1.22 (d, J=7.1 Hz, 3H), 1.20 (d, J=6.1 Hz, 3H), 1.15 (d, J=7.1 Hz, 3H), 1.14 (d, J=7.8 Hz, 3H), 1.02 (d, J=6.7 Hz, 3H), 0.92–0.78 (series of m, 2H), 0.83 (t, J=7.5 Hz, 3H), 0.60–0.53 (m, 2H), 0.50–0.41 (m, 2H), 0.16–0.08 (series of m, 4H); $^{13}$C NMR (75 MHz, CDCl$_3$) δ 216.1, 176.2, 158.1, 157.2, 131.0, 129.9, 113.8, 103.1, 95.9, 82.6, 80.3, 78.8, 77.9, 77.8, 76.3, 72.6, 70.4, 69.0, 65.7, 61.7, 60.4, 55.2, 54.5, 50.7, 49.5, 45.5, 45.4, 45.3, 39.0, 34.8, 32.6, 30.3, 22.0, 21.5, 20.2, 18.9, 18.6, 16.0, 14.2, 14.1, 10.4, 10.3, 9.0, 5.5, 2.7; MS (FAB) (M+H)$^+$ at m/z 987; Anal. Calcd for C$_{54}$H$_{86}$N$_2$O$_{14}$.0.4 H$_2$O: C, 65.22; H, 8.80; N, 2.82. Found: C, 65.23; H, 8.52; N, 2.74.

EXAMPLE 11

3',3'-N-Bisdesmethyl-3',3'-N-biscyclopropylmethyl-11-deoxy-11-[carboxy-(4-fluorophenethylamino)]-6-O-methyl-erthromycin A 11,12-(cyclic carbamate)

The title compound was prepared as described in Example 1 but substituting 4-fluorophenethylamine for 3,4-dichlorophenethylamine. The product was isolated on a silica gel column (3% MeOH/DCM/0.2% NH$_4$OH) as an amorphous solid: mp 207–210° C. (decomp); IR (KBr) υ 3440, 2960, 2930, 2870, 2820, 1755, 1730, 1710, 1505, 1455, 1420, 1375, 1325, 1280, 1230, 1220, 1165, 1125, 1105, 1075, 1065, 1050, 1010, 995 cm$^{-1}$; $^1$H NMR (300 MHz, CDCl$_3$) δ 7.32–7.25 (series of m, 2H), 6.99–6.93 (series of m, 2H), 4.98–4.92 (series of m, 2H), 4.49 (d, J=7.1 Hz, 1H), 4.06–4.00 (m, 1H), 3.87–3.80 (m, 2H), 3.75 (d, J=9.5 Hz, 1H), 3.72 (s, 1H), 3.66 (d, J=7.1 Hz, 1H), 3.53–3.44 (m, 1H), 3.34 (s, 3H), 3.19–3.11 (m, 2H), 3.08 (s, 3H), 3.07–2.81 (series of m, 5H), 2.68–2.56 (series of m, 3H), 2.38 (d, J=15.3 Hz, 1H), 2.23–2.12 (series of m, 3H), 1.98–1.83 (m, 2H), 1.79–1.75 (m, 2H), 1.68–1.48 (series of m, 5H), 1.42 (s, 3H), 1.40 (s, 3H), 1.30 (d, J=6.4 Hz, 3H), 1.25 (s, 3H), 1.23 (d, J=5.4 Hz, 3H), 1.20 (d, J=5.8 Hz, 3H), 1.16 (d, J=5.8 Hz, 3H), 1.14 (d, J=7.4 Hz, 3H), 1.03 (d, J=6.8 Hz, 3H), 0.92–0.81 (series of m, 2H), 0.83 (t, J=7.5 Hz, 3H), 0.62–0.52 (m, 2H), 0.51–0.42 (m, 2H), 0.16–0.08 (series of m, 4H); $^{13}$C NMR (300 MHz, CDCl$_3$) δ 216.2, 176.3, 157.2, 134.7, 130.4, 130.3, 115.2, 114.9, 103.2, 96.0, 82.7, 80.3, 78.9, 78.0, 77.8, 76.3, 72.7, 70.5, 69.1, 65.8, 61.8, 60.5, 54.6, 50.7, 49.5, 45.6, 45.3, 45.2, 39.1, 39.1, 39.0, 34.9, 32.7, 30.4, 22.0, 21.5, 20.2, 18.9, 18.6, 16.0, 14.3, 14.1, 10.4, 10.3, 9.0, 5.5, 2.7; MS (FAB) (M+H)$^+$ at m/z 975.

EXAMPLE 12

3',3'-N-Bisdesmethyl-3',3'-N-biscyclobutyl-11-deoxy-11-[carboxy-(4-chloro-3-fluorophenethylamino)]-O-methl-erythromycin A 11,12-(cyclic carbamate)

The title compound was prepared as described in Example 2 but substituting 4-chloro-3-fluorophenethylamine for 3,4-dichlorophenethylamine. The product was isolated from silica gel chromatography (3% MeOH/DCM/0.2% NH$_4$OH) as an amorphous solid: R$_f$=0.43 (8% MeOH/DCM, 0.1% NH$_4$OH); IR (KBr) υ 3440, 2970, 2940, 2880, 1760, 1735, 1710, 1580, 1495, 1460, 1425, 1380, 1330, 1285, 1240, 1170, 1105, 1070, 1055, 1015, 1000 cm$^{-1}$; $^1$H NMR (300 MHz, CDCl$_3$) δ 7.32–7.26 (m, 1H), 7.16 (dd, J=10.2, 2.1 Hz, 1H), 7.07 (dd, J=8.1, 1.3 Hz, 1H), 4.93–4.88 (m, 2H), 4.40 (d, J=7.1 Hz, 1H), 4.06–3.96 (m, 1H), 3.91–3.70 (series of m, 3H), 3.69 (s, 1H), 3.64 (d, J=7.1 Hz, 1H), 3.51–3.41 (m, 1H), 3.34 (s, 3H), 3.30–3.08 (series of m, 4H), 3.06 (s, 3H), 3.06–2.82 (series of m, 5H), 2.68–2.56 (m, 1H), 2.55–2.44 (m, 1H), 2.37 (d, J=14.9 Hz, 1H), 2.10 (d, J=10.5 Hz, 1H), 2.08–1.81 (series of m, 9H), 1.79–1.72 (m, 2H), 1.68–1.46 (series of m, 9H), 1.42 (s, 3H), 1.40 (s, 3H), 1.29 (d, J=6.1 Hz, 3H), 1.25 (s, 3H), 1.22 (d, J=6.4 Hz, 3H), 1.20 (d, J=5.8 Hz, 3H), 1.15 (d, J=7.8 Hz, 3H), 1.12 (d, J=7.8 Hz, 3H), 1.02 (d, J=6.8 Hz, 3H), 0.82 (t, J=7.5 Hz, 3H); $^{13}$C NMR (300 MHz, CDCl$_3$) δ 216.4, 176.4, 157.2, 140.0, 139.9, 130.3, 125.4, 117.3, 117.0, 103.4, 96.0, 82.8, 80.3, 78.9, 77.9, 77.7, 76.2, 72.6, 70.8, 69.2, 65.7, 60.3, 58.8, 54.4, 50.7, 49.5, 45.6, 45.2, 44.8, 39.0 (2C), 38.9, 34.8, 32.8, 32.5, 31.2, 30.1, 21.9, 21.5, 20.1, 18.9, 18.6, 16.0, 15.7, 14.2, 14.1, 10.2, 9.0; MS (FAB) (M+H)$^+$ at m/z 1009; Anal. Calcd for C$_{53}$H$_{82}$ Cl F N$_2$O$_{13}$: C, 63.05; H, 8.19; N, 2.77. Found: C, 63.06; H, 8.50; N, 2.68.

EXAMPLE 13

3',3'-N-Bisdesmethyl-3',3'-N-biscyclopropylmethyl-11-deoxy-11-[carboxy-(4-chloro-3-fluorophenethylamino)]-6-O-methyl-erythromycin A 11,12-(cyclic carbamate)

The title compound was prepared as described in Example 1 but substituting 4-chloro-3-fluorophenethylamine for 3,4-dichlorophenethylamine. The product was isolated from silica gel chromatography (3% MeOH/DCM/0.2% NH$_4$OH) as an amorphous solid: R$_f$=0.44 (8% MeOH/DCM+0.1% NH$_4$OH); IR (KBr) υ 3440, 2970, 2940, 2880, 1760, 1735, 1715, 1585, 1495, 1460, 1425, 1380, 1330, 1285, 1240, 1170, 1125, 1110, 1090, 1070, 1055, 1015, 1000 cm$^{-1}$; $^1$H NMR (300 MHz, CDCl$_3$) δ 7.32–7.26 (m, 1H), 7.16 (dd, J=10.2, 2.1 Hz, 1H), 7.07 (dd, J=8.1, 1.3 Hz, 1H), 4.94–4.88 (m, 2H), 4.49 (d, J=6.8 Hz, 1H), 4.08–3.98 (m, 1H), 3.92–3.78 (m, 2H), 3.74 (d, J=9.8 Hz, 1H), 3.70 (s, 1H), 3.66 (d, J=7.5 Hz, 1H), 3.54–3.43 (m, 1H), 3.33 (s, 3H), 3.20–3.07 (m, 2H), 3.06 (s, 3H), 3.05–2.82 (series of m, 5H), 2.70–2.56 (m, 3H), 2.34 (d, J=15.6 Hz, 1H), 2.24–2.10 (series of m, 3H), 1.98–1.84 (m, 2H), 1.80–1.72 (m, 2H), 1.71–1.46 (series of m, 5H), 1.42 (s, 3H), 1.40 (s, 3H), 1.30 (d, J=6.1 Hz, 3H), 1.25 (s, 3H), 1.22 (d, J=57.1 Hz, 3H), 1.21 (d, J=5.8 Hz, 3H), 1.16 (d, J=7.1 Hz, 3H), 1.13 (d, J=6.8 Hz, 3H), 1.02 (d, J=6.8 Hz, 3H), 0.91–0.78 (series of m, 2H), 0.82 (t, J=7.3 Hz, 3H), 0.63–0.52 (m, 2H), 0.52–0.41 (m, 2H), 0.18–0.08 (series of m, 4H); $^{13}$C NMR (75 MHz, CDCl$_3$) δ 216.4, 176.4, 159.7, 157.2, 156.3, 140.0, 139.9, 130.3, 125.4, 117.3, 117.0, 103.1, 96.0, 82.8, 80.2, 78.9, 77.9, 77.7, 76.2, 72.6, 70.4, 69.1, 65.8, 61.7, 60.3, 54.5, 50.7, 49.5, 45.6, 45.3, 44.8, 39.0 (2C), 34.8, 32.8, 30.2, 21.9, 21.5, 20.2, 18.9, 18.6, 16.0, 14.2, 14.1, 10.4, 10.2, 9.0, 5.5 (2C), 2.7 (2C); MS (FAB) (M+H)$^+$ at m/z 1009; Anal. Calcd for C$_{53}$H$_{82}$Cl$_1$F$_1$N$_2$O$_{13}$.0.2 C$_6$H$_{14}$.0.2 H$_2$O: C, 63.17; H, 8.33; N, 2.72. Found: C, 63.02; H, 8.63; N, 2.63.

EXAMPLE 14

3',3'-N-Bisdesmethyl-3',3'-N-biscyclobutyl-11-deoxy-11-[carboxy-(3-chloro-4-fluorophenethylamino)]-O-methyl-erythromycin A 11,12-(cyclic carbamate)

The title compound was prepared as described in Example 2 except substituting 3-chloro-4-fluorophenethylamine for 3,4-dichlorophenethylamine: $^1$H NMR (300 MHz, CDCl$_3$) δ 7.39 (dd, J=2, 7 Hz, 1H, Ar H), 7.22–7.19 (m, 1H, Ar H), 7.04 (dd, J=9 Hz, 1H, Ar H), 4.41 (d, J=7 Hz, 1H, C-1' CH), 4.03–4.00 (m, 1H, C-5" CH), 3.74 (d, J=10 Hz, 1H, C-3 CH), 3.70 (s, 1H, C-11 CH), 3.65 (d, J=7 Hz, 1H, C-5 CH), 3.47–3.44 (m, 1H, C-5' CH), 3.34 (s, 3H, C-3" OCH$_3$), 3.08 (s, 3H, C-6 OCH$_3$), 2.64–2.63 (m, 1H, C-8 CH), 2.37 (d, J=15 Hz, 1H, C-2" CH), 2.10 (d, J=10 Hz, 1H, C-4" OH), 1.43 (s, 3H, C-6 CH$_3$), 1.40 (s, 3H, C-12 CH$_3$), 1.30 (d, J=6, 3H, C-6" CH$_3$), 1.15 (d, J=7 Hz, 3H, C-2 CH$_3$), 1.13 (d, J=7 Hz, 3H, C-4 CH$_3$), 1.03 (d, J=7 Hz, 3H, C-10 CH$_3$), 0.83 (t, J=7 Hz, 3H, C-15 CH$_3$); $^{13}$C NMR (CDCl$_3$) δ 216.3, 176.3, 157.7, 157.2, 155.8, 136.0, 136.0, 131.0, 128.6, 128.5, 116.4, 116.2, 103.0, 96.0, 82.8, 80.3, 78.9, 77.9, 77.8, 76.2, 72.6, 70.8, 69.2, 65.7, 60.3, 58.8, 54.3, 50.7, 49.5, 45.6, 45.2, 45.0, 39.0, 39.0, 38.9, 34.8, 32.5, 32.5, 31.2, 30.0, 21.9, 21.5, 20.1, 18.9, 18.6, 16.0, 15.6, 14.2, 14.1, 10.2, 8.9; MS (ESI) (M+H)$^+$ at m/z 1009; Anal. Calcd for C$_{53}$H$_{82}$ClFN$_2$O$_{13}$: C, 63.05; H, 8.19; N, 2.77. Found: C, 62.89; H, 8.14; N, 2.81.

EXAMPLE 15

3',3'-N-Bisdesmethyl-3',3'-N-biscyclopropylmethyl-11-deoxy-11-[carboxy-(3-chloro-4-fluorophenetlamino)]-6-O-methyl-erythromycin A 11,12-(cyclic carbamate)

The title compound was prepared as described in Example 1 except substituting 3-chloro-4-fluorophenethylamine for 3,4-dichlorophenethylamine: $^1$H NMR (300 MHz, CDCl$_3$) δ 7.40 (dd, J=2, 7 Hz, 1H), 7.23–7.20 (m, 1H), 7.05 (dd, J=9 Hz, 1H), 4.95–4.91 (series of m, 2H), 4.50 (d, J=7 Hz, 1H), 4.06–4.02 (m, 1H), 3.90–3.78 (series of m, 2H), 3.76 (d, J=10 Hz, 1H), 3.71 (s, 1H), 3.67 (d, J=7 Hz, 1H), 3.51–3.41 (m, 1H), 3.34 (s, 3H), 3.17–3.12 (series of m, 2H), 3.08 (s, 3H), 3.05–2.84 (series of m, 5H), 2.67–2.60 (series of m, 3H), 2.39 (s, 1H), 2.23–2.19 (series of m, 2H), 2.13 (d, J=10 Hz, 1H), 1.95–1.87 (series of m, 2H), 1.80–1.77 (series of m, 2H), 1.66–1.52 (series of m, 4H), 1.44 (s, 3H), 1.40 (s, 3H), 1.31 (d, J=6 Hz, 3H), 1.26 (s, 3H), 1.24–1.21 (series of m, 6H), 1.17–1.14 (series of m, 6H), 1.03 (d, J=7 Hz, 3H), 0.84 (t, J=7 Hz, 3H), 0.60–0.56 (m, 2H), 0.49–0.45 (m, 2H), 0.14–0.12 (series of m, 4H); $^{13}$C NMR (75 MHz, CDCl$_3$) δ 216.3, 176.3, 157.8, 157.2, 155.8, 136.0, 131.0, 128.6, 128.5, 116.4, 116.2, 103.1, 96.0, 82.8, 80.3, 78.9, 77.9, 77.8, 76.3, 72.7, 70.6, 69.1, 65.8, 61.8, 60.4, 54.5, 50.7, 49.5, 45.6, 45.3, 45.0, 39.1, 39.0, 34.9, 32.5, 30.3, 21.9, 21.5, 20.2, 18.9, 18.6, 16.0, 14.2, 14.1, 10.4, 10.2, 9.0, 5.5, 2.7; MS (ESI) (M+H)$^+$ at m/z 1009; Anal. Calcd for C$_{53}$H$_{82}$ClFN$_2$O$_{13}$.0.25(CH$_2$Cl$_2$): C, 62.04; H, 8.06; N, 2.71. Found: C, 62.44; H, 8.34; N, 2.66.

EXAMPLE 16

3',3'-N-Bisdesmethyl-3'-N-cyclopentyl-3'-N-cyclopropylmethyl-11-deoxy-11-[carboxy-(3-chloro-4-fluorophenethylamino)]-6-O-methyl-erythromycin A 11,12-(cyclic carbamate)

The title compound was prepared as described in Example 5 but substituting cyclopentanone for acetone, cyclopropylcarboxaldehyde for cyclobutanone, and 4-fluoro-3-chlorophenethylamine for 4-chlorophenethylamine; MS (ESI) (M+H)$^+$ at m/z 1095.

EXAMPLE 17

3',3'-N-Bisdesmethyl-3',3'-N-biscyclopropylmethyl-11-deoxy-11-[carboxy-(3,4-difluorophenethylamino)]-6-O-methyl-erytromycin A 11,12-(cyclic carbamate)

The title compound was prepared as described in Example 1 but substituting 3,4-difluorophenethylamine for 3,4-dichlorophenethylamine. The product was crystallized from CH$_3$CN/H$_2$O: mp=209–211° C. (CH$_3$CN/H$_2$O); IR (KBr) υ 3442, 2972, 2938, 2883, 2831, 1761, 1735, 1711, 1609, 1519, 1458, 1424, 1379, 1326, 1282, 1235, 1211, 1167, 1126, 1106, 1089, 1067, 1052, 1012, 1000 cm$^{-1}$; $^1$H NMR (300 MHz, CDCl$_3$) δ 7.22–7.03 (series of m, 3H), 4.95–4.90 (series of m, 2H), 4.49 (d, J=7.1 Hz, 1H), 4.09–3.97 (m, 1H), 3.92–3.79 (m, 2H), 3.74 (d, J=9.5 Hz, 1H), 3.70 (s, 1H), 3.66 (d, J=7.5 Hz, 1H), 3.54–3.44 (m, 1H), 3.34 (s, 3H), 3.18–3.11 (m, 2H), 3.10–2.80 (series of m, 5H), 3.07 (s, 3H), 2.68–2.57 (m, 3H), 2.38 (d, J=15.2 Hz, 1H), 2.23–2.15 (m, 2H), 2.14 (d, J=10.2 Hz, 1H), 1.98–1.74 (series of m, 4H), 1.71–1.47 (series of m, 4H), 1.43 (s, 3H), 1.40 (s, 3H), 1.30 (d, J=6.4 Hz, 3H), 1.25 (s, 3H), 1.23 (d, J=6.1 Hz, 3H), 1.21 (d, J=6.1 Hz, 3H), 1.16 (d, J=6.1 Hz, 3H), 1.14 (d, J=7.1 Hz, 3H), 1.02 (d, J=7.2 Hz, 3H), 0.91–0.80 (series of m, 2H), 0.83 (t, J=7.3 Hz, 3H), 0.62–0.52 (m, 2H), 0.51–0.41 (m, 2H), 0.17–0.07 (series of m, 4H); $^{13}$C NMR (75 MHz, CDCl$_3$) δ 216.29, 176.37, 157.19, 152.5–146.5 (m, 2C), 136.5–135.5 (m, 1C), 125.0–124.7 (m, 1C), 117.9–116.8 (m, 2C), 103.16, 96.02, 82.78, 80.29, 78.94, 77.96, 77.83, 76.27, 72.68, 70.49, 69.08, 65.81, 61.81, 60.44, 54.55 (2C), 50.64, 49.48, 45.59, 45.33, 45.03, 39.12, 39.05, 39.02, 34.89, 32.71, 30.37, 21.97, 21.52, 21.49, 20.18, 18.88, 18.65, 16.01, 14.22, 14.12, 10.40, 10.23, 9.00, 5.48 (2C), 2.69 (2C); MS (FAB) (M+H)$^+$ at m/z 993; Anal. Calcd for C$_{53}$H$_{82}$F$_2$N$_2$O$_{13}$.0.2 H$_2$O: C, 63.86; H, 8.33; N, 2.81. Found: C, 63.87; H, 8.29; N, 2.80.

EXAMPLE 18

3',3'-N-Bisdesmethyl-3',3'-N-biscyclobutyl-11-deoxy-11-[carboxy-(3,4-difluorophenethylamino)]-6-O-methyl-erythromycin A 11,12-(cyclic carbamate)

The title compound was prepared as described in Example 2 but substituting 3,4-difluorophenethylamino for 3,4-dichlorophenethylamine. The product was crystallized from CH$_3$CN/H$_2$O: mp 220–222° C. (CH$_3$CN/H$_2$O); IR (KBr) υ 3446, 2977, 2938, 2883, 1745, 1734, 1713, 1607, 1518, 1459, 1425, 1378, 1327, 1284, 1236, 1168, 1103, 1094, 1070, 1055, 1013, 1001 cm$^{-1}$; $^1$H NMR (300 MHz, CDCl$_3$) δ 7.23–7.03 (series of m, 3H), 4.94–4.89 (series of m, 2H), 4.46 (d, J=7.4 Hz, 1H), 4.07–3.97 (m, 1H), 3.92–3.78 (series of m, 2H), 3.75 (d, J=9.1 Hz, 1H), 3.70 (s, 1H), 3.67 (d, J=7.8 Hz, 1H), 3.54–3.44 (m, 1H), 3.33 (s, 3H), 3.24–3.11 (m, 2H), 3.10–2.80 (series of m, 5H), 3.07 (s, 3H), 2.68–2.55 (m, 2H), 2.47–2.40 (m, 1H), 2.37 (d, J=15.2 Hz, 1H), 2.31 (s, 3H), 2.31–2.19 (m, 1H), 2.15 (d, J=10.1 Hz, 1H), 1.98–1.72 (series of m, 4H), 1.68–1.46 (series of m, 4H), 1.43 (s, 3H), 1.40 (s, 3H), 1.30 (d, J=6.1 Hz, 3H), 1.25 (s, 3H), 1.22 (d, J=6.1 Hz, 3H), 1.22 (d, J=6.1 Hz, 3H), 1.15 (d, J=7.4 Hz, 3H), 1.13 (d, J=7.5 Hz, 3H), 1.02 (d, J=6.8 Hz, 3H), 0.89–0.78 (m, 1H), 0.83 (t, J=7.3 Hz, 3H), 0.58–0.46 (m, 2H), 0.15–0.07 (m, 2H); $^{13}$C NMR (75 MHz, CDCl$_3$) δ 216.35, 176.43, 157.20, 152.5–146.5 (m, 2C), 136.5–135.5 (m, 1C), 125.0–124.7 (m, IC), 117.9–116.8 (m, 2C), 103.02, 96.13, 82.77, 80.19, 78.94, 77.92, 77.89, 76.26, 72.63, 70.55, 68.96, 65.78, 64.61, 60.34, 58.59, 50.67, 49.49, 45.56, 45.30, 44.99, 39.09 (2C), 39.01, 36.91, 34.85, 32.69, 29.42, 21.93, 21.49, 20.18, 18.89, 18.68, 16.03, 14.23, 14.13, 10.25, 10.04, 9.01, 4.41, 3.36; MS (FAB) (M+H)$^+$ at m/z 953; Anal. Calcd for C$_{50}$H$_{78}$ F$_2$ N$_2$O$_{13}$: C, 63.01; H, 8.25; N, 2.94. Found: C, 63.08; H, 8.28; N, 2.89.

EXAMPLE 19

3',3'-N-Bisdesmethyl-3'-N-cyclobutyl-3'-N-cyclopropylmethyl-11-deoxy-11-[carboxy-(3-chloro-4-fluorophenethylamino)]-6-O-methyl-erythromycin A 11,12-(cyclic carbamate) (Compound 25, Scheme 5)

A solution of 140 mg (0.16 mmol) of the compound 23 prepared as described in Example 5 but substituting 3-chloro-4-fluorophenethylamine for 3,4-dichlorophenethylamine was dissolved in 5 mL of methanol and treated with cyclobutanone (20 mg, 0.29 mmol), sodium cyanoborohydride (40 mg, 0.65 mmol) and acetic acid (to pH 5–6) and the mixture stirred at ambient temperature. After 48 h TLC [CHCl$_3$:MeOH, 98:2, Ce (IV) visualization] indicated complete conversion to a new, less polar material. The reaction was concentrated and the resulting residue partitioned between ethyl acetate (150 mL) and NaHCO$_3$ (sat.) (150 mL). The organic layer was washed with NaHCO$_3$ (sat.) (2×150 mL), and brine (150 mL) prior to drying (Na$_2$SO$_4$), filtering and concentrating. The resulting residue was purified on a silica gel column (elution with CHCl$_3$:MeOH, 9:1) to yield 135 mg of 24 (88%): MS (FAB)(M+H)$^+$ at m/z 955.

A solution of 135 mg (0.14 mmol) of 24 was dissolved in 4 mL of methanol and treated with cyclopropanecarboxaldehyde (20 mg, 0.29 mmol), sodium cyanoborohydride (140 mg, 2.3 mmol) and acetic acid (pH 5–6) and the mixture stirred at ambient temperature. After 48 h TLC [CHCl$_3$:MeOH, 98:2, Ce (IV) visualization] indicated complete conversion to a new, less polar material. The reaction was concentrated and the resulting residue partitioned between ethyl acetate (100 mL) and NaHCO$_3$ (sat) (100 mL). The organic layer was washed with NaHCO$_3$ (sat.) (2×150 mL), and brine (100 mL) prior to drying (Na$_2$SO$_4$), filtering and concentrating. The resulting residue was purified on a silica gel column (elution with CHCl$_3$:MeOH, 9:1) to yield the compound 25: MS (FAB)(M+H)$^+$ at m/z 997; Anal. Calcd for C$_{52}$H$_{82}$ClF N$_2$O$_{13}$: C, 63.05; H, 8.19; N, 2.77. Found: C, 62.92; H, 8.13; N, 3.07.

EXAMPLE 20

3',3'-N-Bisdesmethyl-3',3'-N-bis-[3-(2-pyridyl)-propyl]-11-deoxy-11-[carboxy-(3,4-dichlorophenethylamino)]-6-O-methyl-erythromycin A 11,12-(cyclic carbamate)

The title compound was prepared as described in Example 1 but substituting 3-(2-pyridyl)propanal for cyclopropanecarboxaldehyde. The crude product was purified on a silica gel column (CHCl$_3$ to MeOH:CHCl$_3$, 2:98) yielding an amorphous solid. IR (MIC) υ 2970, 2938, 1758, 1734, 1458, 1423, 1168, 1128, 1104, 1067, 1053, 1012, 997 cm$^{-1}$. $^{13}$C (CDCl$_3$) δ 216.34, 176.43, 157.23, 149.68, 147.47, 139.35, 135.86, 132.20, 131.06, 130.30, 128.45, 102.92, 96.23, 82.86, 80.40, 78.92, 78.17, 77.85, 76.26, 72.89, 70.77, 68.89, 65.91, 62.59, 60.36, 50.72, 49.58, 49.27, 45.59, 45.30, 44.84, 39.02, 35.01, 32.66, 30.67, 30.56, 30.40, 21.46, 21.41, 20.21, 18.94, 18.75, 16.07, 14.22, 14.17, 10.28, 9.14. MS (APCI) at m/z 1157 (M+H)$^+$.

EXAMPLE 21

3',3-N-Bisdesmethyl-3'-N-cyclopropylmethyl-3'-N-4-hydroxymethyl-(2-furylmethyl-11-Deoxy-11-[carboxy-(3,4-dichlorophenethylamino)]-6-O-methyl-erythromycin A 11,12-(cyclic carbamate)

The title compound was prepared as described in Example 19 but substituting the compound 15 for the compound 23 and 4-hydroxymethyl-2-furaldehyde for cyclobutanone: MS (FAB) (M+H)$^+$ at m/z 1153.

EXAMPLE 22

3',3'-N-Bisdesmethyl-3'-N-cyclopropylmethyl-3'-N-[3-(4-pyridyl)propyl]-11-deoxy-11-[carboxy-(3,4-dichlorophenethylamino)]-6-O-methyl-erythromycin A 11,12-(cyclic carbamate)

The title compound was prepared as described in Example 21 but substituting 3-(4-pyridyl)-propanal for 4-hydroxymethyl-2-furaldehyde. The crude product was purified on a silica gel column (CHCl$_3$ to MeOH:CHCl$_3$, 2:98) yielding a crystalline solid: mp 115–6° C.; IR (film) υ 3442, 2970, 2937, 1755, 1458, 1168, 1067, 1053, 1011 cm$^{-1}$; $^{13}$C NMR (CDCl$_3$) δ 216.28, 176.33, 157.17, 151.13, 149.49, 139.27, 132.16, 131.02, 130.25, 130.12, 128.38, 123.82, 102.94, 96.04, 82.80, 80.33, 78.87, 77.87, 77.81, 76.25, 72.69, 70.60, 68.94, 65.78, 62.50, 60.34, 55.14, 50.65, 49.47, 48.91, 45.54, 45.27, 44.79, 39.08, 38.99, 34.83, 32.91, 32.61, 30.46, 29.67, 21.90, 21.46, 21.44, 20.17, 18.89, 18.65, 16.03, 14.18, 14.12, 10.23, 9.04, 8.51, 5.38, 2.88; MS (APCI) (M+H)$^+$ at m/z 1090.

EXAMPLE 23

3',3'-N-Bisdesmethyl-3'-N-cyclopropylmethyl-3'-N-(4hydroxymethyl-2-furyl)methyl-11-deoxy-11-[carboxy-(3-chloro-4-fluorophenethylamino)]-6-O-methyl-erythromycin A 11,12-(cyclic carbamate)

The title compound was prepared as described in Example 19 but substituting 4-hydroxymethyl-2-furaldehyde for cyclobutananone: MS (FAB) (M+H)$^+$ at m/z 1137.

EXAMPLE 24

3',3'-N-Bisdesmethyl-3'-N-cyclopropylmethyl-3'-N-(2-furyl)methyl-11-deoxy-11-[carboxy-(3-chloro-4-fluorophenethylamino)]-6-O-methyl-erythromycin A 11,12-(cyclic carbamate)

The title compound was prepared as described in Example 19 but substituting furaldehyde for cyclobutanone: MS (FAB) (M+H)$^+$ at m/z 1107.

EXAMPLE 25

3',3'-N-Bisdesmethyl-3'-N-cyclopropylmethyl-3'-N-(6-methyl-2-pyridyl)methyl-11-deoxy-11-[carboxy-(3-chloro-4-fluorophenethylamino)]-6-O-methyl-erythromycin A 11,12-(cyclic carbamate)

The title compound was prepared as described in Example 19 but substituting 6-methyl-2-pyridylcarboxaldehyde for cyclobutanone: MS (FAB) (M+H)$^+$ at m/z 1132.

EXAMPLE 26

3',3'-N-Bisdesmethyl-3'-N-bis-(1-methylcyclopropyl)methyl-11-deoxy-11-[carboxy-(3-chloro-4-fluorophenethylamino)]-6-O-methyl-erythromycin A 11,12-(cyclic carbamate)

The title compound was prepared as described in Example 15 but substituting 1-methylcyclopropanecarboxaldehyde for cyclopropanecarboxaldehyde: MS (FAB) (M+H)$^+$ at m/z 1036.

EXAMPLE 27

3',3'-N-Bisdesmethyl-3',3'-N-bis-(1-methylcyclopropyl)methyl-11-deoxy-11-[carboxy-(3,4-dichlorophenethylamino)]-6-O-methyl-erythromycin A 11,12-(cyclic carbamate)

The title compound was prepared as described in Example 1 but substituting 1-methylcyclopropanecarboxaldehyde for cyclopropanecarboxaldehyde: MS (FAB) (M+H)$^+$ at m/z 1052.

EXAMPLE 28

3',3'-N-Bisdesmethyl-3'-N-(1-methylcyclopropyl)methyl-3'-N-cyclopropylmethyl-11-deoxy-11-[carboxy-(3-chloro-4fluorophenethylamino)]-6-O-methyl-erythromycin A 11,12-(cyclic carbamate)

The title compound was prepared as described in Example 19 but substituting 1-methylcyclopropanecarboxaldehyde for cyclobutanone: MS (FAB) (M+H)$^+$ at m/z 1022.

EXAMPLE 29

3',3'-N-Bisdesmethyl-3'-N-(1-methylcyclopropyl)methyl-3'-N-cyclopropylmethyl-11-deoxy-11-[carboxy-(3,4-dichlorophenethylamino)]-6-O-methyl-erythromycin A 11,12-(cyclic carbamate)

The title compound was prepared as described in Example 28 but substituting 3,4-dichlorophenethylamine for 3-chloro-4-fluorophenethylamine: MS (FAB) (M+H)$^+$ at m/z 1038.

EXAMPLE 30

3',3'-N-Bisdesmethyl-3'-N-isopropyl-3'-N-cyclopropylmethyl-11-deoxy-11-[carboxy-(3-chloro-4-fluorophenethylamino)]-6-O-methyl-erythromycin A 11,12-(cyclic carbamate)

The title compound was prepared as described in Example 28 but substituting acetone for 1-methylcyclopropanecarboxaldehyde: MS (FAB) (M+H)$^+$ at m/z 996.

EXAMPLE 31

3',3'-N-Bisdesmethyl-3'-N-isopropyl-3'-N-cyclopropylmethyl-11-deoxy-11-[carboxy-(3,4-dichlorophenethylamino)]-6-O-methyl-erythromycin A 11,12-(cyclic carbamate)

The title compound was prepared as described in Example 29 but substituting acetone for 1-methylcyclopropanecarboxaldehyde: MS (FAB) (M+H)$^+$ at m/z 1012.

EXAMPLE 32

3',3'-N-Bisdesmethyl-3'-N-isopropyl-3'-N-(1-methylcyclopropyl)methyl-11-deoxy-11-[carboxy-(3-chloro-4-fluorophenethylamino)]-6-O-methyl-erythromycin A 11,12-(cyclic carbamate)

The title compound was prepared as described in Example 28 but substituting acetone for cyclopropanecarboxaldehyde: MS (FAB) (M+H)$^+$ at m/z 1010.

EXAMPLE 33

3',3'-N-Bisdesmethyl-3'-N-isopropyl-3'-N-(1-methylcyclopropyl)methyl-11-deoxy-11-[carboxy-(3,4-dichlorophenethylamino]-6-O-methyl-erythromycin A 11,12-(cyclic carbamate)

The title compound was prepared as described in Example 29 but substituting acetone for cyclopropanecarboxaldehyde: MS (FAB) (M+H)$^+$ at m/z 1026.

EXAMPLE 34

3',3'-N-bisdesmethyl-3'-N-cyclopropyl-3'-N-isopropyl-11-deoxy-11-[carboxy-(4-chlorophenethylamino)]-6-O-methyl-erytromycin A 11,12-(cyclic carbamate)

The title compound was prepared as described in Example 5 but substituting [(1-ethoxycyclopropyl)oxy]trimethylsilane for cyclobutanone; MS (FAB) (M+H)$^+$ at m/z 965.

EXAMPLES 35–60

The compounds in Examples 35–60 disclosed in Table 3 were prepared according to the methods described in the above Examples.

TABLE 3

| Example | X, Y   | R, R' |
|---------|--------|-------|
| 35      | F, Cl  |       |
| 36      | Cl, Cl |       |
| 37      | F, Cl  |       |
| 38      | Cl, Cl |       |

TABLE 3-continued

| Example | X, Y | R, R' |
|---------|------|-------|
| 39 | F, Cl | (cyclopropylmethyl)N(—)CH(CH2CH2-(4-OH-3-OMe-phenyl)) |
| 40 | Cl, Cl | (cyclopropylmethyl)N(—)CH(CH2CH2-(4-OH-3-OMe-phenyl)) |
| 41 | F, Cl | (1-methylcyclopropylmethyl)N(—)(cyclobutyl) |
| 42 | Cl, Cl | (1-methylcyclopropylmethyl)N(—)(cyclobutyl) |
| 43 | F, Cl | (1-ethylcyclopropylmethyl)N(—)(cyclopropylmethyl) |
| 44 | Cl, Cl | (1-ethylcyclopropylmethyl)N(—)(cyclopropylmethyl) |
| 45 | F, Cl | (1-phenylcyclopropylmethyl)N(—)(cyclopropylmethyl) |
| 46 | Cl, Cl | (1-phenylcyclopropylmethyl)N(—)(cyclopropylmethyl) |
| 47 | F, Cl | (1-methylcyclopropylmethyl)N(—)(ethyl) |
| 48 | Cl, Cl | (1-methylcyclopropylmethyl)N(—)(ethyl) |

TABLE 3-continued

| Example | X, Y | R, R' |
|---------|------|-------|
| 49 | F, Cl | (1-methylcyclopropylmethyl)N(—)(isobutyl) |
| 50 | Cl, Cl | (1-methylcyclopropylmethyl)N(—)(isobutyl) |
| 51 | F, Cl | (1-allylcyclopropylmethyl)N(—)(cyclopropylmethyl) |
| 52 | Cl, Cl | (1-allylcyclopropylmethyl)N(—)(cyclopropylmethyl) |
| 53 | F, Cl | (1-benzylcyclopropylmethyl)N(—)(cyclopropylmethyl) |
| 54 | Cl, Cl | (1-benzylcyclopropylmethyl)N(—)(cyclopropylmethyl) |
| 55 | F, Cl | (cyclobutylmethyl)N(—)(cyclobutylmethyl) |
| 56 | Cl, Cl | (cyclobutylmethyl)N(—)(cyclobutylmethyl) |
| 57 | F, Cl | (cyclopropylmethyl)N(—)(cyclobutylmethyl) |
| 58 | Cl, Cl | (cyclopropylmethyl)N(—)(cyclobutylmethyl) |
| 59 | F, Cl | (isobutyl)N(—)(isobutyl) |

TABLE 3-continued

| Example | X, Y | R, R' |
|---|---|---|
| 60 | Cl, Cl | 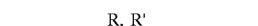 |

We claim:

1. A compound having the formula:

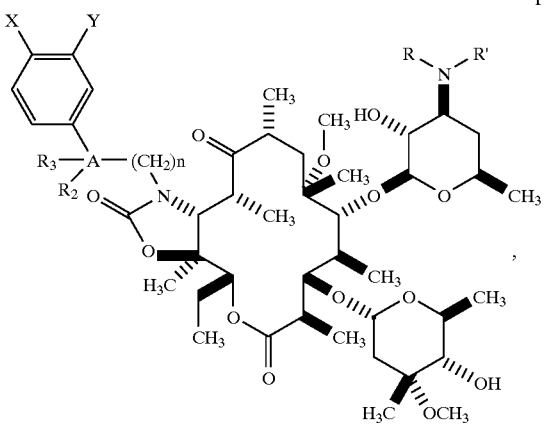

or a pharmaceutically acceptable salt or ester thereof, wherein

A is selected from the group consisting of:
 (a) —C,
 (b) —N, and
 (c) —O;

X and Y are independently at each occurrence selected from the group consisting of:
 (a) hydrogen,
 (b) halide,
 (c) trifluoromethyl,
 (d) alkoxy,
 (e) alkyl,
 (f) aryl, and
 (g) substituted aryl;

R and R' are selected from the group consisting of:
 (a) $C_2$–$C_{20}$ alkyl,
 (b) cycloalkyl,
 (c) heterocycle,
 (d) substituted heterocycle,
 (e) alkylcycloalkyl,
 (f) substituted alkylcycloalkyl,
 (g) alkylaryl,
 (f) alkylheterocycle,
 (g) alkenyl,
 (h) alkynyl,
 (i) —C(S)—$NHR_4$, C($NHR_4$)—$NHR_4$, wherein $R_4$ is hydrogen, alkyl, or aryl; and
 (j) —$(CH_2)_n$—C$(CH_2)_m$—$R_5$, wherein m is 2, 3, 4, or 5, and $R_5$ is alkyl, alkoxy, aryl, or substituted aryl;

$R_2$ and $R_3$ are independently at each occurrence
 (a) hydrogen,
 (b) methyl, or $R_2$ and $R_3$ taken together with A may form a cyclic moiety, when A is C;

$R_3$ is absent when A is N; and n=1, 2 or 3.

2. The compound of claim 1, wherein R is alkyl, alkenyl, cycloalkyl, heterocycle, (heterocyclic)alkyl or alkylcycloalkyl; X and Y are independently at each occurrence chloro, fluoro, dioxalano, hydrogen, or alkoxy; A is —C or N; $R_2$ and $R_3$ are independently at each occurrence hydrogen or together they form cyclopropyl moiety and n is 1.

3. A compound selected from the group consisting of:

3',3'-N-bisdesmethyl-3',3'-N-biscyclopropylmethyl-11-deoxy-11-[carboxy-(3,4-dichlorophenethylamino)]-6-O-methyl-erythromycin A 11,12-(cyclic carbamate);

3',3'-N-bisdesmethyl-3',3'-N-biscyclobutyl-11-deoxy-11-[carboxy-(3,4-dichlorophenethylamino)]-6-O-methyl-erythromycin A 11,12-(cyclic carbamate);

3',3'-N-bisdesmethyl-3',3'--N-biscyclopropylmethyl-11-deoxy-11-[carboxy-(4-chlorophenethylamino)]-6-O-methyl-erythromycin A 11,12-(cyclic carbamate);

3',3'-N-bisdesmethyl-3',3'-N-biscyclobutyl-11-deoxy-11-[carboxy-(4-chlorophenethylamino)]-6-O-methyl-erythromycin A 11,12-(cyclic carbamate);

3',3'-N-bisdesmethyl-3'-N-cyclobutyl-3'-N-isopropyl-11-deoxy-11-[carboxy-(4-chlorophenethylamino)]-6-O-methyl-erythromycin A 11,12-(cyclic carbamate);

3',3'-N-bisdesmethyl-3'-N-isopropyl-3'-N-propyl-11-deoxy-11-[carboxy-(4-chlorophenethylamino)]-6-O-methyl-erythromycin A 11,12-(cyclic carbamate);

3',3'-N-bisdesmethyl-3'-N-cyclopropylmethyl-3'-N-isopropyl-11-deoxy-11-[carboxy-(4-chlorophenethylamino)]-6-O-methyl-erythromycin A 11,12-(cyclic carbamate);

3',3'-N-bisdesmethyl-3'-N-ethyl-3'-N-isopropyl-11-deoxy-11-[carboxy-(4-chlorophenethylamino)]-6-O-methyl-erythromycin A 11,12-(cyclic carbamate);

3',3'-N-bisdesmethyl-3'-N-cyclobutylmethyl-3'-N-cyclopropylmethyl-11-deoxy-11-[carboxy-(4-chlorophenethylamino)]-6-O-methyl-erythromycin A 11,12-(cyclic carbamate);

3',3'-N-biscyclopropylmethyl-11-deoxy-11-[carboxy-(4-methoxyphenethylamino)]-6-O-methyl-erythromycin A 11,12-(cyclic carbamate);

3',3'-N-bisdesmethyl-3',3'-N-biscyclopropylmethyl-11-deoxy-11-[carboxy-(4-fluorophenethylamino)]-6-O-methyl-erythromycin A 11,12-(cyclic carbamate);

3',3'-N-bisdesmethyl-3',3'-N-biscyclobutyl-11-deoxy-11-[carboxy-(4-chloro-3-fluorophenethylamino)]-O-methyl-erythromycin A 11,12-(cyclic carbamate);

3',-N-bisdesmethyl-3',3'-N-biscyclopropylmethyl-11-deoxy-11-[carboxy-(4-chloro-3-fluorophenethylamino)]-6-O-methyl-erythromycin A 11,12-(cyclic carbamate);

3',3'-N-bisdesmethyl-3',3'-N-biscyclobutyl-11-deoxy-11-[carboxy-(3-chloro-4-fluorophenethylamino)]-O-methyl-erythromycin A 11,12-(cyclic carbamate);

3',3'-N-bisdesmethyl-3',3'-N-biscyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopentyl-3'-N-cyclopropylmethyl-11-deoxy-11-[carboxy-(3-chloro-4-difluorophenethylamino)]-6-O-methyl-erythromycin A 11,12-(cyclic carbamate);

3',3'-N-bisdesmethyl-3',3'-N-biscyclopropylmethyl-11-deoxy-11-[carboxy-(3,4-difluorophenethylamino)]-6-O-methyl-erythromycin A 11,12-(cyclic carbamate);

3',3'-N-bisdesmethyl-3',3'-N-biscyclobutyl-11-deoxy-11-[carboxy-(3,4-difluorophenethylamino)]-6-O-methyl-erythromycin A 11,12-(cyclic carbamate);

3',3'-N-bisdesmethyl-3'-N-cyclobutyl-3'-N-cyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3',3'-N-bis[3-(3-pyridyl)propyl]-11-deoxy-11-[carboxy-(3-chloro-4-fluorophenethylamino)]-6-O-methyl-erythromycin A 11,12-(cyclic carbamate);

3',3'-N-bisdesmethyl-3'-N-biscyclopropylmethyl-3'-N-(4-hydroxymethyl-2-furyl)methyl-11-deoxy-11-[carboxy-(3-chloro-4-fluorophenethylaminno)]-6-O-methyl-erythromycin A 11,12-(cyclic carbamate);

3',3'-N-bisdesmethyl-3'-N-cyclopropylmethyl-3'-N-[3-(4-pyridyl)propyl]-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-[4-(hydroxymethyl-2-furyl)]methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(2-furyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-[6-methyl-(2-pyridyl)]methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-bis-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-bis-(1-methylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-(1-methylcyclopropyl)methyl-3'-N-cyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-(1-methylcyclopropyl)methyl-3'-N-cyclopropylmethyl-11-deoxy-11-[carboxy-(3,4-dichlorophenethylamino)]-6-O-methyl-erythromycin A 11,12-(cyclic carbarnate);

3',3'-N-bisdesmethyl-3'-N-isopropyl-3'-N-cyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isopropyl-3'-N-cyclopropylmethyl-11-deoxy-11-[carboxy-(3,4-dichlorophenethylamino)]-6-O-methyl-erythromycin A 11,12-(cyclic carbamate);

3',3'-N-bisdesmethyl-3'-N-isopropyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isopropyl-3'-N-(1-methylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-cyclopropylmethyl-3'-N-(biscyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(biscyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(2,2-dimethylpropyl)-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(2,2-dimethylpropyl)-11-deoxy-11-[carboxy-(3,4dichlorophenethylamino)]-6-O-methyl-erythromycin A 11,12-(cyclic carbamate);

3',3'-N-bisdesmethyl-3'-N-cyclopropylmethyl-3'-N-[3-(4-hydroxy-3-methoxyphenyl)-11-methyl]propyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-[3-(4-hydroxy-3-methoxyphenyl)-1-methyl]propyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclobutyl-3'-N-(1-methylcyclopropyl)methyl-11-deoxy-11-[carboxy-(3-chloro-4fluorophenethylamino)]-6-O-methyl-erythromycin A 11,12-(cyclic carbamate);

3',3'-N-bisdesmethyl-3'-N-cyclobutyl-3'-N-(1-methylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-ethylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-ethylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(11-phenylcyclopropyl)methyl-11-3deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-phenylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-ethyl-3'-N-(1-methylcyclopropyl)methyl-11-deoxy-11-[carboxy-(3-chloro-4fluorophenethylamino)]-6-O-methyl-erythromycin A 11,12-(cyclic carbamate);

3',3'-N-bisdesmethyl-3'-N-ethyl-3'-N-(1-methylcyclopropyl)methyl-11-deoxy-11-[carboxy-(3,4dichlorophenethylamino)]-6-amethyl-erythromycin A 11,12-(cyclic carbamate);

3',3'-N-bisdesmethyl-3'-N-isobutyl-3'-N-(1-methylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-isobutyl-3'-N-(1-methylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-cyclopropylmethyl-3'-N-(1-allylcyclopropyl)methyl-11-deoxy-11-[carboxy-(3- chloro-4-fluorophenethylamino)]-6-O-methyl-erythromycin A 11,12-(cyclic carbamate);

3',3'-N-bisdesmethyl-3'-N-cyclopropylmethyl-3'-N-(1-allylcyclopropyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-benzylcyclopropyl)methyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-cyclopropylmethyl-3'-N-(1-benzylcyclopropyl)methyl-11-deoxy-11-[carboxy-(3,4dichlorophenethylamino)]-6-O-methyl-erythromycin A 11,12-(cyclic carbamate);

3',3'-N-bisdesmethyl-3'-N-bis-(1-methylcyclobutyl)methyl-11-deoxy-11-[carboxy-(3-chloro-4fluorophenethylamino)]-6-O-methyl-erythromycin A 11,12-(cyclic carbamate);

3',3'-N-bisdesmethyl-3'-N-bis-(1-methylcyclobutyl)methyl-11-deoxy-11-[carboxy-(3,4-dichlorophenethylamino)]-6-O-methyl-erythromycin A 11,12-(cyclic carbamate);

3',3'-N-bisdesmethyl-3'-N-cyclopropylmethyl-3'-N-(1-methylcyclobutyl)methyl-11-deoxy-11-[carboxy-(3-chloro-4-fluorophenethylamino)]-6-O-methyl-erythromycin A 11,12-(cyclic carbamate); and 3',3'-N-bisdesmethyl-3'-N-cyclopropylmethyl-3'-N-(1-methylcyclobutyl)methyl-11-deoxy-11-[carboxy-(3,4-dichlorophenethylamino)]-6-O-methyl-erythromycin A 11,12-(cyclic carbamate).

4. The compound according to claim 3, selected from the group consisting of:

3',3'-N-bisdesmethyl-3'-N-biscyclopropylmethyl-11-deoxy-11-[carboxy-(3-chloro-4-fluorophenethylamino)]-6-O-methyl-erythromycin A 11,12-(cyclic carbamate);

3',3'-N-bisdesmethyl-3'-N-biscyclobutyl-11-deoxy-11-[carboxy-(3-chloro-4-fluorophenethylamino)]-6-O-methyl-erythromycin A 11,12-(cyclic carbamate).

3',3'-N-bisdesmethyl-3',3'-N-bis-(1-methylcyclopropyl)methyl-1-deoxy-11-[carboxy-(3, chloro-4fluorophenethylamino)]-6-O-methyl-erythromycin A 11,12-(cyclic carbamate); and 3',3'-N-bisdesmethyl-3'-N-isopropyl-3'-N-(1-methylcyclopropyl)methyl-11-deoxy-11-[carboxy-(3-chloro-4fluorophenethylamino)]-6-O-methyl-erythromycin A 11,12-(cyclic carbamate).

5. A pharmaceutical composition for inhibiting the release of LH comprising a therapeutically effective amount of a compound according to claim 1 in combination with a pharmaceutically acceptable carrier.

6. A method of inhibiting LH release in a mammal in need of such treatment comprising administering to the mammal a therapeutically-effective amount of a compound according to claim 1.

7. A process for preparing a compound represented by the formula:

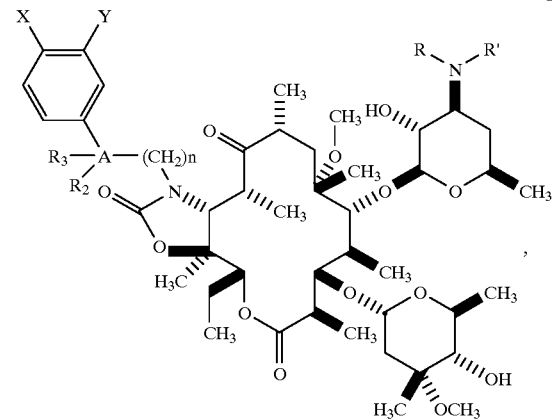

or a pharmaceutically acceptable salt or ester thereof, wherein

A is selected from the group consisting of:
(a) —C,
(b) —N, and
(c) —O;

X and Y are independently at each occurrence selected from the group consisting of:
(a) hydrogen,
(b) halide,
(c) trifluoromethyl,
(d) alkoxy,
(e) alkyl,
(f) aryl, and
(g) substituted aryl;

R and R' are selected from the group consisting of:
(a) $C_2$–$C_{20}$ alkyl,
(b) cycloalkyl,
(c) heterocycle,
(d) substituted heterocycle,
(e) alkylcycloalkyl,
(f) substituted alkylcycloalkyl,
(g) alkylaryl,
(f) alkylheterocycle,
(g) alkenyl,
(h) alkynyl,
(i) —C(S)—$NHR_4$, C($NR_4$)—$NHR_4$, wherein $R_4$ is hydrogen, alkyl, or aryl; and
(j) —$(CH_2)_n$—$C(CH_2)_m$—$R_5$, wherein m is 2, 3, 4, or 5, and $R_5$ is alkyl, alkoxy, aryl or substituted aryl;

$R_2$ and $R_3$ are independently at each occurrence
(a) hydrogen,
(b) methyl, or $R_2$ and $R_3$ taken together with A may form a cyclic moiety, when A is C;

$R_3$ is absent when A is N; and n=1, 2 or 3;

comprises the steps of:

(a) reacting a compound of formula:

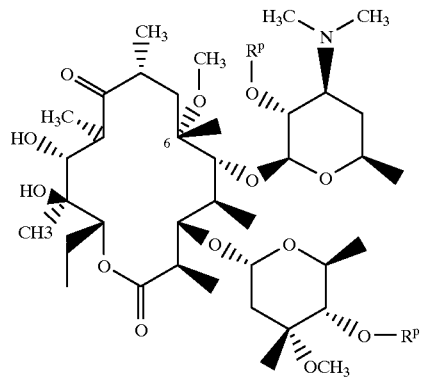

wherein Rp is a hydroxy-protecting group, with sodium hexamethyldisilazide and carbonyldiimidazole to afford a compound of the formula:

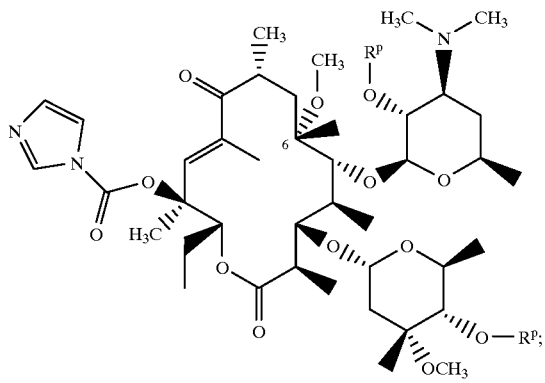

(b) reacting the compound obtained in step (a) with an amino compound of the formula:

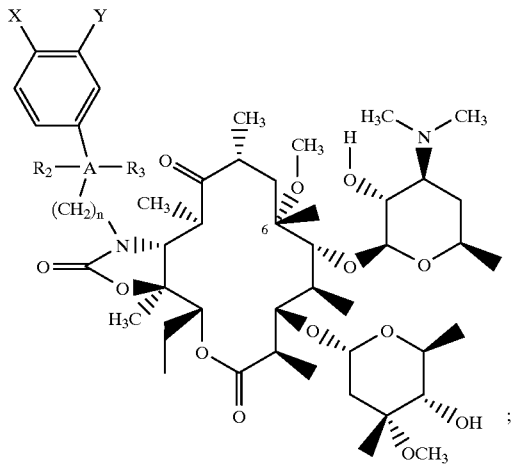

(c) stepwise desmethylating the 3'-amino by treating the compound obtained in step (b) with iodine in presence of a base to afford a compound of the formula:

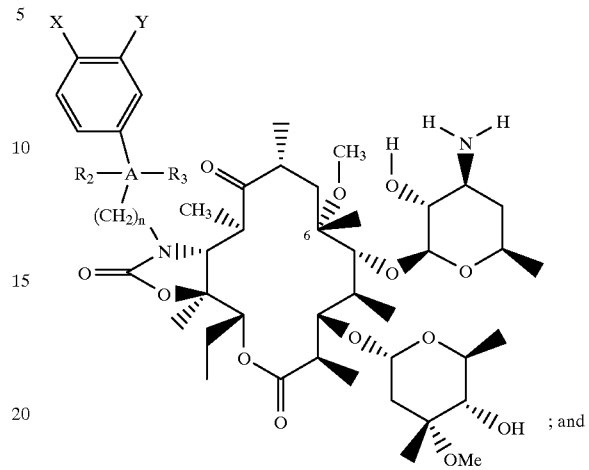
; and (d) alkylating the 3',3'-N-bisdesmethylated compound obtained in step (c) with an alkylating agent.

8. The process according to claim 7, wherein the reaction in step (a) is carried out in an aprotic solvent at 0 to 25° C.

9. The process according to claim 7, wherein the reaction in step (b) is carried out without solvent or in acetonitrile at 25 to 80° C.

10. The process according to claim 7, wherein the desmethylation is carried out by reaction of the compound obtained in step (b) with iodine in the presence of a base and a light or heat source.

11. The process according to claim 7, wherein the desmethylation is carried out by reaction of the compound obtained in step (b) with a chloroformate selected from the group consisting of benzyl chloroformate, allyl chloroformate and vinyl chloroformate.

12. The process according to claim 7, wherein the alkylation in step (d) is achieved by reaction of the compound obtained in step (c) with an aldehyde or ketone in the presence of a hydride metal or in the presence of Pd/C catalyst in a protic or non-protic solvent under hydrogen.

13. The process according to claim 7, wherein the alkylation in step (d) is achieved by reaction of the compound obtained in step (c) with an alkyl halide in presence of a base.

14. The process of claim 7, wherein R is alkyl, alkenyl, cycloalkyl, heterocycle, (heterocyclic)alkyl or alkylcycloalkyl; X and Y are independently at each occurrence chloro, fluoro, dioxalano, hydrogen, or alkoxy; A is —C; $R_2$ and $R_3$ are independently at each occurrence hydrogen or together they form cyclopropyl moiety and n is 1.

15. The process of claim 7, wherein the alkylating agent is cyclopentanone and the alkylation is carried out in the presence of sodium cyanoborohydride in methanol.

16. The process for preparing a compound according to claim 1, wherein the process comprises the steps of:

(a) reacting a compound of formula:

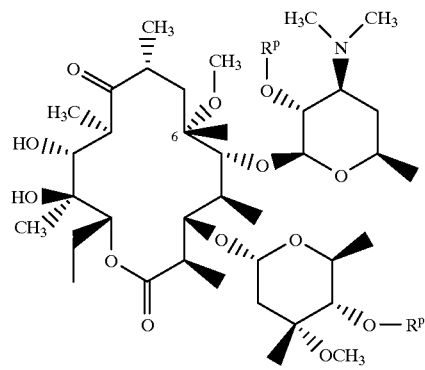

wherein Rp is a hydloxy-protecting group, with sodium hexamethyldisilazide and carbonyldiimidazole to afford a compound of the formula:

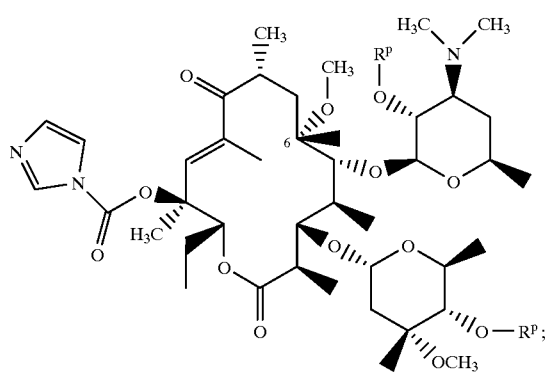

(b) reacting the compound obtained in step (a) with a compound an amino compound of the formula:

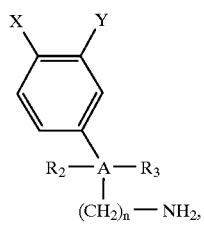

followed by deprotection of the 2',4"-hydroxy protected groups to afford a compound of the formula:

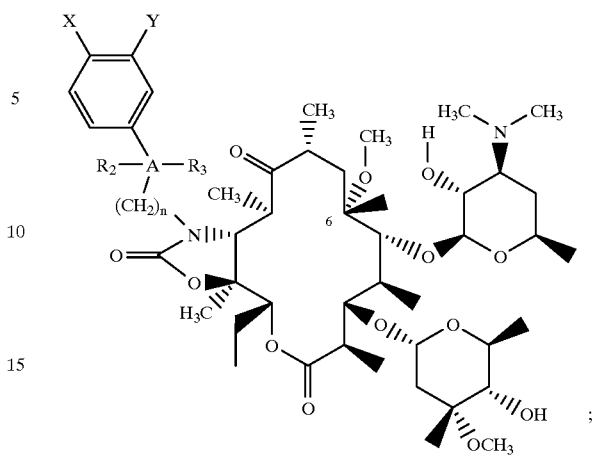

(c) selectively desmethylating the compound obtained in step (b) to obtain the compound of the formula:

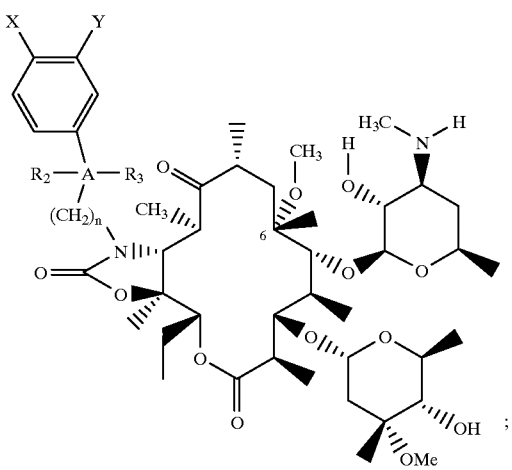

(d) alkylating the 3'-N-desmethylated compound obtained in step (c) with an alkylating agent to afford a compound of the formula:

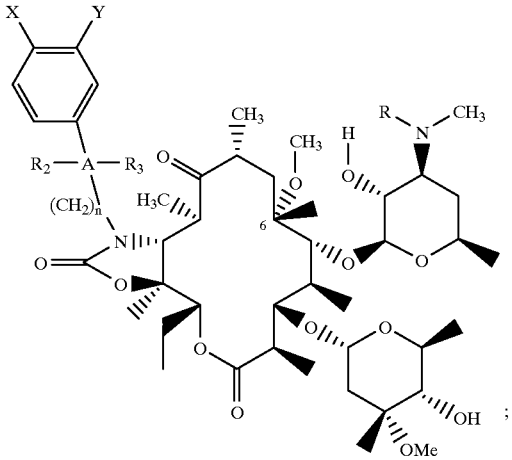

(e) desmethylating the 3'-amino by treating the compound obtained in step (d) with iodine in presence of a base to afford a compound of the formula:
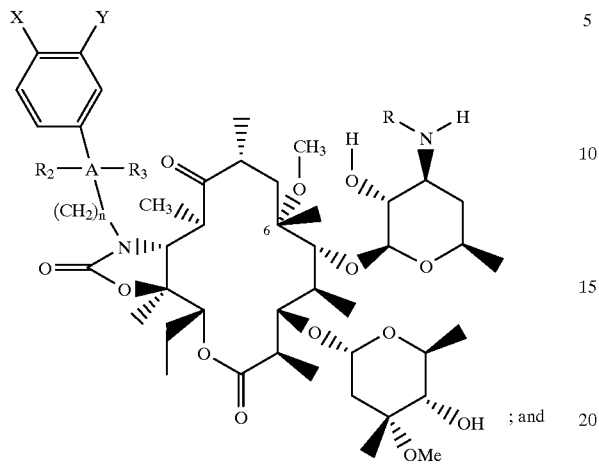
; and
(f) alkylating the 3'-N-desmethylated compound obtained in step (e) with an alkylating agent.
* * * * *

UNITED STATES PATENT AND TRADEMARK OFFICE
CERTIFICATE OF CORRECTION

PATENT NO. : 5,972,898
DATED : October 26, 1999
INVENTOR(S) : Daryl R. Sauer et al.

It is certified that error appears in the above-identified patent and that said Letters Patent is hereby corrected as shown below:

Column 47,
Line 59, replace "C(NHR4)" with -- C(NR4) --.

Column 48,
Line 40, replace "3',3'-N-biscyclopropylmethyl" with -- 3',3'-N-bisdesmethyl-3',3'n-biscyclopropylmethyl --.
Line 50, replace "3',-N-bisdesmethyl" with -- 3',3'-N-bisdesmethyl --.

Column 49,
Line 14, replace "fluorophenethylaminno" with -- fluorophenethylamino --.
Line 49, replace "carbarnate" with -- carbamate --.
Line 64, replace "4dichlorophenethylamino" with -- 4-dichlorophenethylamino --.

Column 50,
Line 13, replace "4dichlorophenethylamino" with -- 4-dichlorophenethylamino --.
Line 16, replace "11-methyl" with -- 1-methyl --.
Line 41, replace "11-phenylcyclopropyl" with -- 1-phenylcyclopropyl --.
Line 42, replace "11-3deoxy-11" with -- 11-deoxy-11 --.
Line 56, replace "4dichlorophenethylamino" with -- 4-dichlorophenethylamino --.
Line 56, replace "6-amethyl" with -- 6-0-methyl --.
Line 64, replace "4dichlorophenethylamino" with -- 4-dichlorophenethylamino --.

Column 51,
Line 15, replace "4dichlorophenethylamino" with -- 4-dichlorophenethylamino --.
Line 20, replace "4fluorophenethylamino" with -- 4-fluorophenethylamino --.
Line 49, replace "1-deoxy" with -- 11-deoxy --.
Lines 50 and 55, replace "4fluorophenethylamino" with -- 4-fluorophenethylamino --.

UNITED STATES PATENT AND TRADEMARK OFFICE
CERTIFICATE OF CORRECTION

PATENT NO. : 5,972,898
DATED : October 26, 1999
INVENTOR(S) : Daryl R. Sauer et al.

It is certified that error appears in the above-identified patent and that said Letters Patent is hereby corrected as shown below:

<u>Column 55,</u>
Line 20, replace "hydloxy-protecting" with -- hydroxy-protecting --.

Signed and Sealed this

Twenty-eighth Day of January, 2003

JAMES E. ROGAN
*Director of the United States Patent and Trademark Office*